US008288590B2

(12) United States Patent
Kohn et al.

(10) Patent No.: US 8,288,590 B2
(45) Date of Patent: Oct. 16, 2012

(54) N-SUBSTITUTED MONOMERS AND POLYMERS

(75) Inventors: Joachim B. Kohn, Piscataway, NJ (US); Durgadas Bolikal, Edison, NJ (US); Jaap Schut, Rotterdam (NL); Ernest G. Baluca, San Diego, CA (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/183,051

(22) Filed: Jul. 14, 2011

(65) Prior Publication Data

US 2011/0269848 A1 Nov. 3, 2011

Related U.S. Application Data

(62) Division of application No. 11/873,979, filed on Oct. 17, 2007, now Pat. No. 8,008,528.

(60) Provisional application No. 60/852,471, filed on Oct. 17, 2006.

(51) Int. Cl.
C07C 233/00 (2006.01)
C07C 215/00 (2006.01)
C07C 39/24 (2006.01)
C08G 65/32 (2006.01)
C08G 75/00 (2006.01)
A61K 49/04 (2006.01)
A61K 47/30 (2006.01)

(52) U.S. Cl. ........ 564/170; 564/361; 568/774; 528/172; 528/203; 528/208; 525/408; 514/772.3; 424/9.45

(58) Field of Classification Search .......... 564/170; 568/774; 514/772.3; 525/408; 528/172, 528/203, 208

See application file for complete search history.

(56) References Cited

U.S. PATENT DOCUMENTS

| | | |
|---|---|---|
| 3,251,806 A | 5/1966 | Parker et al. |
| 3,598,859 A | 8/1971 | Yates et al. |
| 4,638,045 A | 1/1987 | Kohn et al. |
| 4,733,665 A | 3/1988 | Palmaz |
| 4,740,207 A | 4/1988 | Kreamer |
| 4,748,982 A | 6/1988 | Horzewski et al. |
| 4,762,129 A | 8/1988 | Bonzel |
| 4,863,735 A | 9/1989 | Kohn et al. |
| 4,877,030 A | 10/1989 | Beck et al. |
| 4,954,126 A | 9/1990 | Wallsten |
| 4,980,449 A | 12/1990 | Kohn et al. |
| 5,007,926 A | 4/1991 | Derbyshire |
| 5,040,548 A | 8/1991 | Yock |
| 5,059,211 A | 10/1991 | Stack et al. |
| 5,061,273 A | 10/1991 | Yock |
| 5,092,877 A | 3/1992 | Pinchuk |
| 5,099,060 A | 3/1992 | Kohn et al. |
| 5,108,416 A | 4/1992 | Ryan et al. |
| 5,140,094 A | 8/1992 | Kohn et al. |
| 5,151,100 A | 9/1992 | Abele et al. |
| 5,158,548 A | 10/1992 | Lau et al. |
| 5,192,307 A | 3/1993 | Wall |
| 5,194,570 A | 3/1993 | Kohn et al. |
| 5,197,987 A | 3/1993 | Koch et al. |
| 5,198,507 A | 3/1993 | Kohn et al. |
| 5,216,115 A | 6/1993 | Kohn et al. |
| 5,219,564 A | 6/1993 | Zalipsky et al. |
| 5,230,349 A | 7/1993 | Langberg |
| 5,232,445 A | 8/1993 | Bonzel |
| 5,242,399 A | 9/1993 | Lau et al. |
| 5,242,997 A | 9/1993 | Kohn et al. |
| 5,263,991 A | 11/1993 | Wiley et al. |
| 5,264,537 A | 11/1993 | Kohn et al. |
| 5,300,085 A | 4/1994 | Yock |
| 5,306,286 A | 4/1994 | Stack et al. |
| 5,344,426 A | 9/1994 | Lau et al. |
| 5,350,395 A | 9/1994 | Yock |
| 5,423,321 A | 6/1995 | Fontenot |
| 5,441,515 A | 8/1995 | Khosravi et al. |
| 5,443,477 A | 8/1995 | Marin et al. |
| 5,443,500 A | 8/1995 | Sigwart |
| 5,445,646 A | 8/1995 | Euteneuer et al. |
| 5,449,382 A | 9/1995 | Dayton |
| 5,451,233 A | 9/1995 | Yock |
| 5,466,439 A | 11/1995 | Gibby et al. |
| 5,469,867 A | 11/1995 | Schmitt |
| 5,490,962 A | 2/1996 | Cima et al. |
| 5,496,275 A | 3/1996 | Sirhan et al. |
| 5,496,346 A | 3/1996 | Horzewski et al. |
| 5,527,337 A | 6/1996 | Stack et al. |
| 5,545,135 A | 8/1996 | Iacob et al. |
| 5,545,138 A | 8/1996 | Fugoso et al. |
| 5,549,556 A | 8/1996 | Ndondo-Lay et al. |
| 5,549,662 A | 8/1996 | Fordenbacher |
| 5,587,507 A | 12/1996 | Kohn et al. |
| 5,618,299 A | 4/1997 | Khosravi et al. |
| 5,626,600 A | 5/1997 | Horzewski et al. |
| 5,641,861 A | 6/1997 | Dooley et al. |
| 5,658,995 A | 8/1997 | Kohn et al. |
| 5,660,822 A | 8/1997 | Poiani et al. |
| 5,670,602 A | 9/1997 | Kohn et al. |
| 5,733,328 A | 3/1998 | Fordenbacher |

(Continued)

FOREIGN PATENT DOCUMENTS

JP 49-002917 A 1/1974

(Continued)

OTHER PUBLICATIONS

Boger, et al. "Studies on the Total Synthesis of Bouvardin and Deoxybouvardin: Cyclic Hexapeptide Cylization Studies and Preparation of Key Partial Structures," Journal of Organic Chemistry 53: 487-499. (1988).

(Continued)

Primary Examiner — Sikarl Witherspoon
(74) Attorney, Agent, or Firm — Fox Rothschild LLP

(57) ABSTRACT

Biocompatible, bioresorbable polymers comprising a plurality of monomeric repeating units containing an amide group, wherein said amide groups are N-substituted and the N-substituent and degree of N-substitution are effective to lower the melt viscosity, the solution viscosity, or both, compared to the same polymer without N-substitution.

26 Claims, No Drawings

U.S. PATENT DOCUMENTS

| | | | |
|---|---|---|---|
| 5,735,872 | A | 4/1998 | Carpenter et al. |
| 5,741,293 | A | 4/1998 | Wijay |
| 5,749,888 | A | 5/1998 | Yock |
| 5,755,708 | A | 5/1998 | Segal |
| 5,769,868 | A | 6/1998 | Yock |
| 5,800,393 | A | 9/1998 | Sahota |
| 5,836,965 | A | 11/1998 | Jendersee et al. |
| 5,868,747 | A | 2/1999 | Ochoa et al. |
| 5,876,419 | A | 3/1999 | Carpenter et al. |
| 5,910,816 | A | 6/1999 | Fontenot et al. |
| 5,912,225 | A | 6/1999 | Mao et al. |
| 5,919,897 | A | 7/1999 | Dooley et al. |
| 5,984,963 | A | 11/1999 | Ryan et al. |
| 5,989,280 | A | 11/1999 | Euteneuer et al. |
| 6,007,545 | A | 12/1999 | Venturelli |
| 6,015,424 | A | 1/2000 | Rosenbluth et al. |
| 6,033,436 | A | 3/2000 | Steinke et al. |
| 6,036,715 | A | 3/2000 | Yock |
| 6,048,521 | A | 4/2000 | Kohn et al. |
| 6,096,782 | A | 8/2000 | Audia et al. |
| 6,103,255 | A | 8/2000 | Levene et al. |
| 6,109,785 | A | 8/2000 | Ross et al. |
| 6,120,491 | A | 9/2000 | Kohn et al. |
| 6,200,338 | B1 | 3/2001 | Solomon et al. |
| RE37,160 | E | 5/2001 | Kohn et al. |
| 6,224,626 | B1 | 5/2001 | Steinke |
| 6,238,687 | B1 | 5/2001 | Mao et al. |
| 6,280,473 | B1 | 8/2001 | Lemperle et al. |
| 6,284,862 | B1 | 9/2001 | Kohn et al. |
| 6,319,492 | B1 | 11/2001 | Kohn et al. |
| 6,375,669 | B1 | 4/2002 | Rosenbluth et al. |
| 6,388,043 | B1 | 5/2002 | Langer et al. |
| 6,409,752 | B1 | 6/2002 | Boatman et al. |
| 6,409,755 | B1 | 6/2002 | Vrba |
| RE37,795 | E | 7/2002 | Kohn et al. |
| 6,447,508 | B1 | 9/2002 | Sharkey et al. |
| 6,475,477 | B1 | 11/2002 | Kohn et al. |
| 6,492,462 | B2 | 12/2002 | Bitler et al. |
| 6,530,958 | B1 | 3/2003 | Cima et al. |
| 6,544,453 | B2 | 4/2003 | Taft et al. |
| 6,550,480 | B2 | 4/2003 | Feldman et al. |
| 6,562,021 | B1 | 5/2003 | Derbin et al. |
| 6,562,958 | B1 | 5/2003 | Breton et al. |
| 6,599,448 | B1 | 7/2003 | Ehrhard, Jr. et al. |
| 6,602,497 | B1 | 8/2003 | Kohn et al. |
| 6,623,521 | B2 | 9/2003 | Steinke et al. |
| 6,652,572 | B2 | 11/2003 | Kugler et al. |
| 6,689,153 | B1 | 2/2004 | Skiba |
| 6,831,116 | B2 | 12/2004 | Bitler et al. |
| 6,852,308 | B2 | 2/2005 | Kohn et al. |
| 6,932,930 | B2 | 8/2005 | DeSimone et al. |
| 7,056,493 | B2 | 6/2006 | Kohn et al. |
| 8,008,528 | B2 | 8/2011 | Kohn et al. |
| 2001/0046505 | A1 | 11/2001 | Kohn et al. |
| 2003/0163187 | A1 | 8/2003 | Weber |
| 2004/0086458 | A1 | 5/2004 | Kohn et al. |
| 2004/0086461 | A1 | 5/2004 | Kohn et al. |
| 2004/0086462 | A1 | 5/2004 | Kohn et al. |
| 2004/0127970 | A1 | 7/2004 | Saunders et al. |
| 2004/0191175 | A1 | 9/2004 | Kohn et al. |
| 2005/0106119 | A1 | 5/2005 | Brandom et al. |
| 2005/0123481 | A1 | 6/2005 | Kohn et al. |
| 2005/0165203 | A1 | 7/2005 | Kohn et al. |
| 2006/0020324 | A1 | 1/2006 | Schmid et al. |
| 2006/0024266 | A1 | 2/2006 | Brandom et al. |
| 2006/0034769 | A1 | 2/2006 | Kohn et al. |
| 2006/0036316 | A1 | 2/2006 | Zeltinger et al. |
| 2006/0115449 | A1 | 6/2006 | Pacetti |
| 2006/0204440 | A1 | 9/2006 | Kohn et al. |

FOREIGN PATENT DOCUMENTS

| | | | |
|---|---|---|---|
| JP | 2010507011 A | 3/2010 | |
| RU | 2009118386 A | 11/2010 | |
| WO | 9640208 A1 | 12/1996 | |
| WO | 9846286 A1 | 10/1998 | |
| WO | 9924391 A1 | 5/1999 | |
| WO | 2004089415 A2 | 10/2004 | |
| WO | 2004089416 A2 | 10/2004 | |
| WO | 2004089470 A2 | 10/2004 | |
| WO | 2006014596 A1 | 2/2006 | |
| WO | 2006020616 A1 | 2/2006 | |

OTHER PUBLICATIONS

Inoue, et al. "A Synthesis of D,L-N,N-Dimethylcycloisoditryosines: A Comment on the Stereochemistry of Previously Reported Intermediates Realted to the Synthesis of RA-VII and Deoxybouvardin," Journal of Organic Chemistry 61: 3936-3937. (1996).

Benzina, et al. "A versatile three-iodine molecular building block leading to new radiopaque polymeric biomaterials," Journal of Biomedical Materials Research 32: 459-466. (1996).

Bates et al. "Solution Forms of Bouvardin and Relatives from NMR Studies, 6-O-Methylbouvardin." Journal of the American Chemical Society 105: 1343-1347. (1983).

Kai et al. "Macrocyclization by TTN Oxidation for the Synthesis of Chloropeptin Left-hand Segment." Tetrahedron Letters 40: 6289-6292. (1999).

Sen Gupta et al. "Properties of L-tyrosine based polyphosphates pertinent to potential biomaterial applications." Polymer 46: 2133-2140. (2005).

Imai et al. "Radical Scavenging Activity and Cytotoxicity of Phenethyl Ether and Cinnamic Amide Derivatives". Anticancer Research 22: 1661-1666. (2002).

Eckert et al. "Exploring Peptide-likeness of Active Molecules Using 2D Fingerprint Methods". J. Chem. Inf. Model 47: 1366-1378. (2007).

Aharoni, et al., "Rigid Backbone Polymers. 2. Polyisocyanates and Their Liquid-Crystal Behavior" Macromolecules, 12 (1):94-103 (1979).

Andruzzi, et al., "Studies on Comb-like Polymers. 2. Poly(octadecylethylene oxide)" Macromolecules, 13:15-18(1980).

Aurelio, et al., "Synthetic Preparation of N-Methyl-a-amino Acids", American Chemical Society, Chem. Rev. 104,5823-5846 (2004).

Cabasso, et al., "Radiopaque Miscible Systems Composed of Poly(Methyl Methacrylate) and Transition and Nontransition Metal Salts: Spectroscopic, Thermal, and Radiographic Characterization" Journal ofApplied Polymer Science, 38:1653-1666 (1989).

Cabasso, et al., "Radiopaque Polymers Based on Acrylated Phosphonate Esters Derived from Polyols" Journal of Applied Polymer Science, 41:3025-3042(1990).

Chupov, et al., "Structure and Physico-Chemical Properties of Comb-Like Polypeptides Based on Poly-L-Lysine" Polymer Science U.S.S.R. 21:241-252 (1979).

Fukuyama, et al., "2- and 4-Nitrobenzenesulfonamides: Exceptionally Versatile Means for Preparation of Secondary Amines and Protection ofAmines" Terahedron Letters, Elsevier Science Ltd., vol. 36, No. 36, DD. 6373-6374 (1995).

Fukuyama, et al., "2,4-Dinitrobenzenesulfonamides: A Simple and Practical Method for the Preparation of a Variety of Secondary Amines and Diamines", Tetrahedron Letters, Elsevier Science Ltd., vol. 38, No. 33. pp. 5831-5834 (1997).

Gonzalez, et al. Side-Chain Crystallinity, Heat of Melting, and Thermal Transitions in poly[N-(10-n-Alkyloxycarbonyl-n-Decyl)Maleimides] (PEMI) Journal of Polymer Science: Polymer Physics Edition. 18:2197-2207 (1980).

Greenberg, et al., "Side Chain Crystallization of n-Alkyl Polymethacrylates and Polyacrylates" Institute of Polymer Research, Polytechnic Institute of Brooklyn. 76:6280-6285. (1954).

Hooper, et al., "Diphenolic monomers derived form the natural amino acid alpha-l-tyrosine: an evaluation of peptide coupling techniques" Journal of Bioactive and Compatible Polymers, 10(4):327-340 XP002045571.

Hutmacher et al., "Scaffold-based tissue engineering: rationale for computer-aided design and solid free-form fabrication systems," TRENDS in Biotechnology vol. 22 No. 7, Jul. 2004, pp. 354-362.

Jayakrishnan, et al., "Synthesis and Polymerization of Some Iodine-Containing Monomers for Biomedical Applications" Journal of Applied Polymer Science 44:743-748 (1992).

Jordan, et al., "Side-Chain Crystallinity. I. Heats of Fusion and Melting Transitions on Selected Homopolymers Having Long Side Chains" Journal of Polymer Science: Part A-1, 9:1835-1852 (1971).

N-SUBSTITUTED MONOMERS AND POLYMERS

CROSS-REFERENCE TO RELATED APPLICATIONS

This application is a divisional of U.S. patent application Ser. No. 11/873,979, filed on Oct. 17, 2007, now U.S. Pat. No. 8,008,528, which claims priority under 35 U.S.C. §119(e) to U.S. Provisional Patent Application Ser. No. 60/852,471, filed on Oct. 17, 2006 and entitled "N-Substituted Monomers and Polymers," and also claims priority under 35 U.S.C. §120 to International Application No. PCT/US07/81571 designating the United States and filed on Oct. 16, 2007. The contents of the foregoing applications are hereby incorporated by reference in their entireties.

BACKGROUND OF THE INVENTION

1. Field of the Invention

This invention relates to N-substituted monomers and polymers, methods of making such monomers and polymers, and methods of using them in various applications, such as medical devices.

2. Description of the Related Art

The tyrosine-derived monomers of U.S. Pat. No. 5,099,060 polymerize to form polymers with higher melt or solution viscosities that may result in poor processibility. As a result, the fabrication of the polymers requires higher temperatures, higher pressures, or both, that are less economical and may also degrade the polymer or any additives (such as biological or pharmaceutical moieties).

Such higher melt or solution viscosities can occur with tyrosine-derived polymers such as the polyiminocarbonates of U.S. Pat. No. 4,980,449, the polycarbonates of U.S. Pat. No. 5,099,060, the polyarylates of U.S. Pat. No. 5,216,115, the poly(alkylene oxide) block copolymers of U.S. Pat. No. 5,658,995, the phosphorous-containing polymers of U.S. Pat. Nos. 5,912,225 and 6,238,687, the anionic polymers of U.S. Pat. No. 6,120,491, the poly(amide carbonates) and poly(ester amides) of U.S. Pat. No. 6,284,862, the radio-opaque polymers of U.S. Pat. No. 6,475,477, and the polyethers of U.S. Pat. No. 6,602,497. The disclosures of all the foregoing patents are incorporated herein by reference in their entirety.

There exists a need for polymers with lower melt viscosities that are capable of being melt-processed and/or solution processed with greater ease, lower temperatures and/or pressures.

SUMMARY OF THE INVENTION

This need is met by the present invention. It has now been discovered that the amide bonds present in tyrosine-derived biocompatible polymers are involved in inter-chain hydrogen bonding, which can interfere in the thermal processibility of the polymer because hydrogen bonding between polymer chains increases melt or solution viscosity. In turn this has lead to the discovery that the effect due to hydrogen bonding in monomers and polymers with peptide linkages can be significantly reduced by replacing the hydrogen atom on the amide nitrogen with methyl or other alkyl groups.

It has surprisingly been discovered that replacing the amide hydrogen with a non-hydrogen-bonding substituent eliminates or greatly reduces this source of intermolecular interaction to a degree such that polymer solubility in organic solvents increases, melt viscosity decreases, and the polymer glass transition likewise decreases. These changes in polymer properties can be so profound that some polymers that were initially non-processible can now be processed by a variety of fabrication technologies, including solvent casting, wet and melt spinning, compression molding, extrusion, and injection molding.

Consequently, an N-substituted version of the polymer may be processed at lower temperatures (e.g., relative to the polymer glass transition temperature or $T_g$) with less thermal/oxidative degradation. This opens the temperature processing window for the polymer, e.g., higher $T_g$ polymers can be processed at existing process temperatures and similar $T_g$ polymers may be processed at lower temperatures.

Likewise, polymers solvated in relatively non-polar solvents, such as dichloromethane, can be processed at higher solids concentrations with lower solution viscosities.

Therefore, according to one aspect of the present invention, biocompatible, bioresorbable polymers are provided comprising a plurality of monomeric repeating units containing an amide group, wherein the amide groups are N-substituted and the N-substituent and degree of N-substitution are effective to lower the melt viscosity, the solution viscosity, or both compared to the same polymer without N-substitution. According to one embodiment, the N-substituents and degree of N-substitution are effective to reduce the melt viscosity, the solution viscosity, or both, at least about 5%, and in another embodiment the reduction is at least about 10%. According to another embodiment, the N-substituents are $C_1$-$C_6$ alkyl groups. According to yet another embodiment, the N-substituent is a methyl group. According to another embodiment, the present invention includes polymers with one or more recurring units of formula (I):

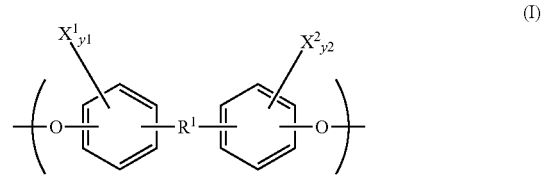

wherein $X^1$ and $X^2$ in formula (I) are each independently selected from Br and I; y1 and y2 in formula (Ia) are each independently zero or an integer in the range of 1 to 4, and $R^1$ is selected from substituted or unsubstituted, saturated or unsaturated, straight chain or branched aliphatic groups containing up to 48 carbon atoms, substituted or unsubstituted aromatic groups containing up to 48 carbon atoms, and substituted or unsubstituted araliphatic groups containing up to 48 carbon atoms in which the aliphatic portions are straight chain or branched and saturated or unsaturated, and $R^1$ contains from 2 to 8 heteroatoms selected from O, S and N, in which two of the heteroatoms form a polymer backbone amide group that is N-substituted. Additional heteroatoms are present when the $R^1$ group contains poly(alkylene oxide) groups.

Unless otherwise defined for a specific embodiment, N-substituted amines are substituted with a substituted or unsubstituted, straight or branched, saturated or unsaturated aliphatic group containing up to 30 carbon atoms, a substituted or unsubstituted aromatic group containing up to 30 carbon atoms, and a substituted or unsubstituted araliphatic group containing up to 30 carbon atoms in which the aliphatic portion is straight chain or branched and saturated or unsaturated. According to one embodiment, $R^1$ groups contain between about 18 and about 36 carbon atoms. According to another embodiment, the N-substituents are $C_1$-$C_6$ alkyl groups. According to yet another embodiment, the N-substituent is a methyl group.

According to one embodiment, $R^1$ has a pendant carboxylic acid group or a pendant carboxylic acid ester or N-substituted amide. According to an embodiment $R^1$ has a pendant N-substituted tertiary amine. According to one embodiment, $R^1$ has both a pendant carboxylic acid group or a pendant carboxylic acid ester or N-substituted amide and a pendant N-substituted tertiary amine. According to another embodiment, $R^1$ in formula (I) is:

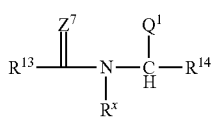

(II)

in which $R^{13}$ and $R^{14}$ each independently contain from 0 to 8 carbons atoms, inclusive, and are independently selected from (—$CHR^1$)$_e$—CH=CH—($CHR^1$—)$_e$ and (—$CHR^1$)$_f$(—$CHNQ^2$)$_g$(—$CHR^1$)$_f$, wherein $R^1$ is H or lower alkyl, each e independently ranges between 0 and 6, inclusive, each f independently ranges between 0 and 8, inclusive and g is 0 or 1; $Z^7$ is O or S; $R^x$ is selected from optionally substituted branched or unbranched $C_1$-$C_{30}$ alkyl and optionally substituted $C_6$-$C_{30}$ aryl; $Q^1$ is C(=$Z^5$)—$R^8$, wherein $Z^5$ is O or S; $Q^2$ is —N($R^x$)$_2$ or N(1V$Q^1$); $R^8$ is selected from H, a therapeutically active moiety, a poly(alkylene oxide), $X_3$-$C_l$-$C_{18}$ alkyl, $X_3$-alkenyl, $X_3$-alkynyl, —$X_5$-cycloalkyl, —$X_5$-heterocyclyl, —$X_5$-aryl and —$X_5$-heteroaryl;

$X_3$ is selected from a bond, O, S, and N-alkyl; $X_4$ is selected from O, S and N-alkyl; and $X_5$ is selected from a bond, lower alkyl, O, S and N-alkyl.

Alkyl, alkenyl, alkynyl, cycloalkyl, heterocyclyl, aryl and heteroaryl groups, except when otherwise defined, contain up to 30 carbon atoms. According to an embodiment, the groups contain up to 18 carbon atoms. Lower alkyl groups, except when otherwise defined, are straight or branched and contain up to 6 carbon atoms. Alkyl, alkenyl and alkynyl, groups are also straight or branched and contain from 0 to eight heteroatoms, and lower alkyl groups also contain 0, 1 or 2 heteroatoms. Heteroatoms are independently selected from O, S and N-lower alkyl. Heterocyclyl and heteroaryl groups also contain from one to eight heteroatoms selected from O, S and N-lower alkyl.

According to one embodiment the poly(alkylene oxide) $R^8$ groups include alkyl-terminated poly(alkylene oxides) of molecular weight 100 to 10,000, examples of which include methoxy-terminated poly(ethylene glycols) (PEG), methoxy-terminated poly(propylene glycols) (PPG), and methoxy-terminated block copolymers of PEG and PPG. According to another embodiment poly(alkylene oxide) groups have a molecular weight between about 400 and about 4000. According to another embodiment the poly(alkylene oxides) are poly(ethylene glycols) with molecular weights between about 1000 and about 2000.

According to another embodiment, one or both aromatic rings may be substituted with from 1 to 4 groups independently selected from halogen, lower alkyl, carboxyl, nitro, thioether, sulfoxide and sulfonyl as long as the substitution patterns are chemically feasible. Any combination of substituents containing more than two nitro substituents is potentially explosive and expressly excluded from these teachings. Monomers and polymers with a sufficient number of aromatic rings sufficiently substituted with bromine or iodine are inherently radio-opaque. In preferred radio-opaque monomers and polymers, at least one monomeric aromatic ring is substituted with iodine, so that the sum of y1 and y2 in formula (I) is greater than zero, preferably on at least one and more preferably on both ring positions ortho to the phenolic oxygen. Preferably both aromatic rings are iodine-substituted at both ortho positions.

According to yet another embodiment, $R^1$ in formula (I) is selected from:

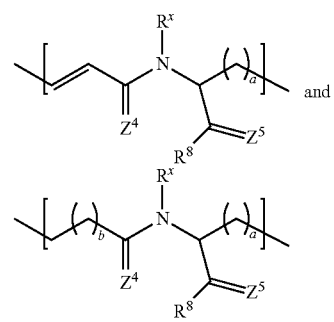

wherein $R^x$ and $R^8$ are the same as described above with respect to formula II; a and b range from 0 and 8, inclusive, and $Z^4$ and $Z^5$ are each independently O or S. According to more specific embodiments, a=1 and b=2.

Polymers according to the present invention include polycarbonates, polyarylates, polyiminocarbonates, polyphosphazenes and polyphosphoesters having the structure of formula (Ia),

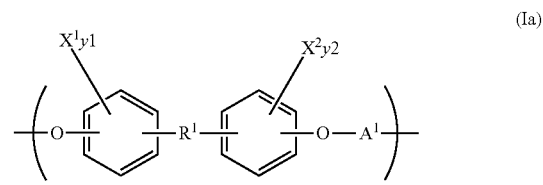

(Ia)

wherein $X^1$, $X^2$, y1, y2 and $R^1$, and the embodiments thereof, are the same as described above with respect to formula (I) and $A^1$ is selected from:

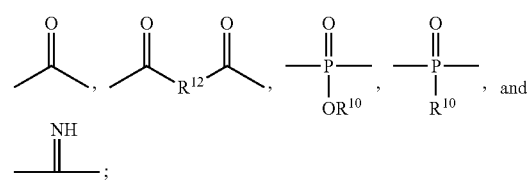

wherein $R^{1o}$ is selected from H, $C_1$-$C_{30}$ alkyl, alkenyl or alkynyl and $C_2$-$C_{30}$ heteroalkyl; heteroalkenyl or heteroalkynyl, and $R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylary or heteroalkynylaryl, $C_6$-$C_{30}$ alkylaryl, alkenylaryl or alkynylaryl, and $C_5$-$C_{30}$ heteroaryl.

In an embodiment, $R^x$ is a branched or unbranched $C_1$-$C_6$ alkyl. In a specific embodiment, $R^x$ is methyl. In an embodiment, $Q^1$ is a group having the structure:

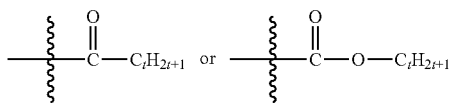

wherein t in the above groups is independently in the range of zero to about 18.

A polymer comprising a recurring unit of formula (I) can be copolymerized with any number of other recurring units. In an embodiment, the polymer comprising a recurring unit of formula (I) further comprises a recurring polyalkylene oxide block units of the formula (III):

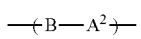  (III)

wherein B is $-O-((CHR^6)_p-O)_q-$; each $R^6$ is independently H or $C_1$ to $C_3$ alkyl; p is an integer ranging between about one and about four; q is an integer ranging between about five and about 3000; and $A^2$ is the same as $A^1$ in formula (Ia). One block copolymerized polymer embodiment contains a molar fraction of alkylene oxide between about 0.1 and about 25%. Another embodiment contains a molar fraction of alkylene oxide between about 0.5 and about 10%. Yet another embodiment contains a molar fraction of alkylene oxide between about 1 and about 5%.

N-substituted polymers according to the present invention are polymerized from diphenols corresponding to the structure of formula (I) prepared according to the methods disclosed by the above-referenced U.S. Pat. No. 5,099,060, the entire disclosure of which is incorporated herein by reference. The polymers can be copolymerized with diphenols that are not N-substituted. Polymers according to the present invention contain embodiments in which the molar fraction of N-substituted monomer is between about 1 and about 50%. Another embodiment provides polymers with a molar fraction of N-substituted monomer between about 5 and about 25%. Yet another embodiment provides polymers with a molar fractin of N-substituted monomer between about 7.5 and about 12.5%.

N-substituted diphenol compounds thus represent new and useful compounds according to the present invention. The present invention therefore also includes diphenol compounds with amide groups that are N-substituted. One embodiment includes diphenol compounds in which the N-substituent is a $C_1$-$C_6$ alkyl group. Another embodiment includes diphenol compounds having the structure of formula (IV):

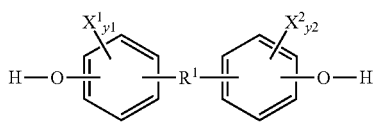  (IV)

wherein $X^1$, $X^2$, y1, y2 and $R^1$, and the embodiments thereof, are the same as described above with respect to formula (I).

According to one diphenol embodiment, $R^1$ is selected so the Formula IV monomer is an N-substituted dityrosine such as the N,N-dimethyl dityrosine depicted below formed by N-methylation of the dityrosine depicted below:

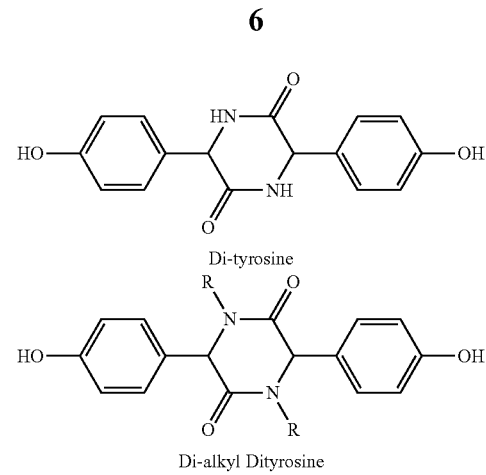

Dityrosines and their preparation are reported in the literature, and dityrosines can be N-substituted by the procedures disclosed herein. The present invention also includes Formula I and Formula Ia polymers polymerized from the N-substituted dityrosines of the present invention.

In general, polymers according to the present invention possess excellent physical properties and melt processability and can be shaped into different three-dimensional structures for specific uses by conventional polymer-forming techniques such as extrusion and injection molding. The solvent-casting and compression molding techniques described in earlier patents disclosing polymers polymerized from tyrosine-derived diphenol compounds can also be used. Therefore, according to another aspect of the present invention, blood-contacting or tissue-implantable medical devices are provided, formed from the polymers of the present invention. Preferably, the devices are formed by thermal fabrication. Such devices include hernia repair devices.

According to one embodiment of this aspect of the invention, the medical device is a stent for treatment of a body lumen. Preferred stents are formed from or coated with radio-opaque polymers according to the present invention, so that fluoroscopic imaging can be used to guide positioning of the device. A preferred radio-opaque, bioresorbable stent according to one embodiment of the present invention is formed from a bioresorbable polymer with sufficient halogen atoms to render the stent inherently visible by X-ray fluoroscopy during stent placement.

According to another aspect of this embodiment of the present invention, the medical device is an embolotherapy product. Embolotherapy products according to the present invention are particulate formulations of biocompatible, bioresorbable polymers according to the present invention. In a preferred embodiment, the polymer contains a sufficient number of halogen atoms to render the embolotherapy product inherently radio-opaque.

Other specific applications for which the polymers of the present invention are also particularly useful include scaffolds for tissue engineering on which isolated cell populations may be transplanted in order to engineer new tissues. The polymers are formed into porous devices as described by Mikos et al., Biomaterials, 14, 323-329 (1993) or Schugens et al., J. Biomed. Mater. Res., 30, 449-462 (1996) or U.S. Pat. No. 6,103,255 to allow for the attachment and growth of cells as described in Bulletin of the Material Research Society, Special Issue on Tissue Engineering (Guest Editor: Joachim Kohn), 21(11), 22-26 (1996). Therefore, another aspect of the present invention provides a tissue scaffold having a porous structure for the attachment and proliferation of cells either in vitro or in vivo formed from polymers according to the present invention.

Another specific application includes implantable drug delivery devices where a pharmaceutically active moiety is admixed within the polymeric matrix for slow release, including devices for ophthalmic drug delivery. Therefore, in one embodiment of the present invention, the polymers are combined with a quantity of a biologically or pharmaceutically active compound sufficient to be therapeutically effective as a site-specific or systemic drug delivery system as described by Gutowska et al., J. Biomater. Res., 29, 811-21 (1995) and Hoffman, J. Controlled Release, 6, 297-305 (1987). Furthermore, another aspect of the present invention provides a method for site-specific or systemic drug delivery by implanting in the body of a patient in need thereof an implantable drug delivery device containing a therapeutically effective amount of a biologically or a physiologically active compound in combination with a polymer of the present invention.

Polymers in accordance with the present invention may be prepared having good film-forming properties. An important phenomena observed for the polymers of the present invention having poly(alkylene oxide) block copolymer segments is the temperature dependent phase transition of the polymer gel or the polymer solution in aqueous solvents. As the temperature increases, the gel of the polymers undergo a phase transition to a collapsed state, while polymer solutions precipitate at a certain temperature or within certain temperature ranges. The polymers of the present invention having poly(alkylene oxide) segments, and especially those that undergo a phase transition at about 30 to 40° C. on heating can be used as biomaterials for drug release and clinical implantation materials. Specific applications include films and sheets for the prevention of adhesion and tissue reconstruction.

Therefore, in another embodiment of the present invention, poly(alkylene oxide) block copolymers of polymers according to the present invention may be formed into a sheet or a coating for application to exposed injured tissues for use as barrier for the prevention of surgical adhesions as described by Urry et al., Mat. Res. Soc. Symp. Proc., 292, 253-64 (1993). Therefore, another aspect of the present invention provides a method for preventing the formation of adhesions between injured tissues by inserting as a barrier between the injured tissues a sheet or a coating of the radio-opaque poly(alkylene oxide) block copolymers of polymers according to the present invention.

The poly(alkylene oxide) segments decrease the surface adhesion of the polymers of the present invention. As the molar fraction of poly(alkylene oxide) increases, the surface adhesion decreases. Polymer coatings containing poly(alkylene oxide) segments according to the present invention may thus be prepared that are resistant to cell attachment and are useful as non-thrombogenic coatings on surfaces in contact with blood. Such polymers also resist bacterial adhesion in this and in other medical applications as well. The present invention therefore includes blood contacting devices and medical implants having surfaces coated with the poly(alkylene oxide) block copolymers of the present invention.

The coated surfaces are preferably polymeric surfaces. Methods according to the present invention include implanting in the body of a patient a blood-contacting device or medical implant having a surface coated with the polymers of the present invention containing poly(alkylene oxide) block copolymer segments.

By varying the molar fraction of poly(alkylene oxide) segments in the block copolymers of the present invention, the hydrophilic/hydrophobic ratios of the polymers can be attenuated to adjust the ability of the polymer coatings to modify cellular behavior. Increasing levels of poly(alkylene oxide) inhibits cellular attachment, migration and proliferation, while increasing the amount of pendent free carboxylic acid groups promotes cellular attachment, migration and proliferation. Therefore, according to yet another aspect of the present invention, a method is provided for regulating cellular attachment, migration and proliferation by contacting living cells, tissues, or biological fluids containing living cells with the polymers of the present invention.

Through pendant free carboxylic acid groups, derivatives of biologically and pharmaceutically active compounds, including drugs, can be attached to the polymer backbone by covalent bonds linked to the carboxylic acid pendent chain. This provides for the sustained release of the biologically or pharmaceutically active compound by means of hydrolysis of the covalent bond between the drug and the polymer backbone. The present invention therefore also includes polymer embodiments in which R is a biologically or pharmaceutically active compound covalently attached to the polymer backbone.

In addition, polymers of the present invention with pendent carboxylic acid groups have a pH dependent dissolution rate. This further enables the polymers to be used as coatings in gastrointestinal drug release carriers to protect some biologically and pharmaceutically active compounds such as drugs from degrading in the acidic environment of the stomach. The copolymers of the present invention having a relatively high concentration of pendent carboxylic acid groups are stable and water insoluble in acidic environments but dissolve/degrade rapidly when exposed to neutral or basic environments. By contrast, copolymers of low acid to ester ratios are more hydrophobic and will not degrade/resorb rapidly in either basic or acidic environments. Therefore, another aspect of the present invention provides a controlled drug delivery system in which a biologically or pharmaceutically active agent is physically coated with a polymer of the present invention having free carboxylic acid groups.

Other features of the present invention will be pointed out in the following description and claims, which disclose the principles of the invention and the best modes which are presently contemplated for carrying them out.

DETAILED DESCRIPTION OF PREFERRED EMBODIMENTS

The present invention introduces a novel class of monomers and copolymers polymerized therefrom in which amino acids or amino acid structural derivatives are linked together to form new monomers are then polymerized to form the new, useful polymers depicted in formula (I). The diphenol monomers of formula IV are prepared following standard procedures of peptide chemistry such as disclosed in J. P. Greenstein and M. Winitz, Chemistry of the Amino Acids, (John Wiley & Sons, New York 1961) and Bodanszky, Practice of Peptide Synthesis (Springer-Verlag, New York, 1984).

Specifically, carbodiimide-mediated coupling reactions in the presence of hydroxybenzotriazole according to the procedure disclosed in U.S. Pat. No. 5,587,507 and U.S. Pat. No. 5,670,602, the disclosures of both of which are hereby incorporated by reference. Suitable carbodiimides are disclosed therein. The preferred carbodiimide is 1-ethyl-3-(3-dimethylamino-propyl)carbodiimide hydro-chloride (EDCI.HCl). The crude monomers can be recrystallized twice, first from 50% acetic acid and water and then from a 20:20:1 ratio of ethyl acetate, hexane and methanol, or, alternatively, flash chromatography on silica gel is used, employing a 100:2 mixture of methylene chloride:methanol as the mobile phase.

Thioamide monomers ($Z^5=S$) can be prepared using the method described by A. Kjaer (Acta Chemica Scandinavica, 6, 1374-83 (1952)). The amide group in the monomers or polymers can also be converted to thioamide groups using the fluorous analog of the Lawesson's reagent ($f_6LR$) whose structure appears below (Kaleta, Z., et al., Org. Lett., 8(8), 1625-1628 (2006)). The second method is preferable, since it allows the formation of the monomer first then allows the conversion of the amide group to the thioamide group.

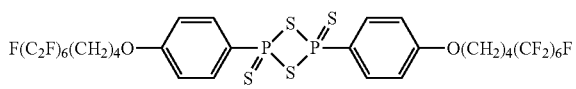

Fluorous Lawesson's Reagent ($f_6LR$)

Treatment of an amide with this reagent in 1:1 molar ratio in THF gives the corresponding thioamide in >88% yield after purification by chromatography or other means.

For the conversion of the tyrosine derived amide monomers to the corresponding thioamides, the phenolic groups of the monomers are first protected by converting them to the diacetyl esters as shown for $I_2DTE$ by treating with $Ac_2O$/pyridine. The O-protected $I_2DTE$ is then reacted with $f_6LR$ followed by base hydrolysis to the thioamide—$I_2DTE$ as shown in the scheme. The transformation can also be carried out on the polymer using similar procedure.

Scheme. Conversion of the amide group in the monomer to the thioamide group

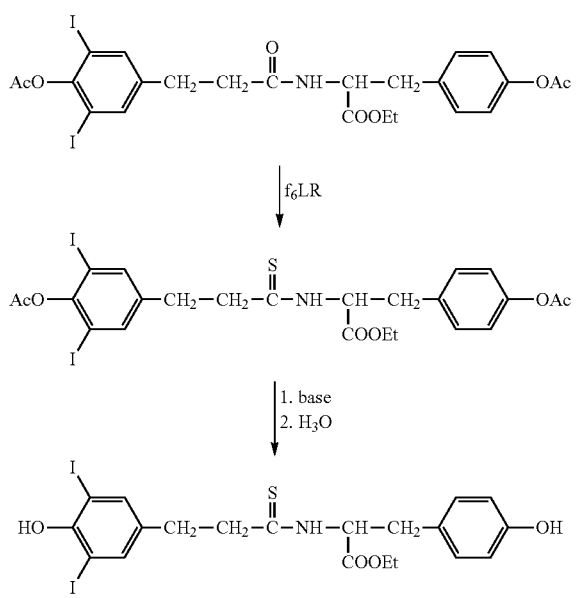

The N-substituted monomers and polymers of the present invention can be prepared by substituting commercially-available N-substituted starting materials for the starting materials of monomers containing amide groups, such as the monomers disclosed by U.S. Pat. No. 5,099,060, or by N-substituting monomers containing amide groups, such as the monomers prepared according to U.S. Pat. No 5,099,060 using non-N-substituted starting materials. There are several methods described in the scientific literature that accomplishes such conversions. For example, the acidic hydrogens of amide groups can be replaced by alkyl groups in the monomer by reacting the monomer or polymer with paraformaldehyde followed by hydrogenation using $Pd/C/H_2$ or using sodium cyanoborohydride.

Provided herein is a method for making N-alkyl/N-aryl monomer precursors of formula AA-1. Those having ordinary skill in the art, guided by the disclosure herein, can use the N-alkylation/N-arylation steps of forming a monomer precursor described herein to create any N-alkylated/N-arylated monomer that corresponds to the polymers described above.

N-Substituted Monomer Preparation

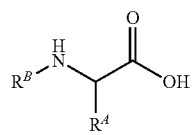

AA-1

The monomer precursors of formula AA-1 are readily prepared via several divergent synthetic routes with the particular route selected relative to the ease of compound preparation, the commercial availability of starting materials, and the like. In some embodiment, the compounds of formula AA-1 can be synthesized as disclosed in U.S. Pat. No. 6.096,782 to Audia et al.; Aurelio et al. (Aurelio et al. "Synthetic Preparation of N-Methyl-α-amino Acids", Chem. Rev., 2004, 5823-5846); Fukuyama et al. (Fukuyama et al. "2,4-Dinitrobenzenesulfonamides: A Simple and Practical Method for the Preparation of a Variety of Secondary Amines and Diamines", Tet. Lett., 1997, 5831-5834); and Ma et al. (Ma et al., "CuI-Catalyzed Coupling Reaction of β-Amino Acids or Esters with Aryl Halides at Temperature Lower Than That Employed in the Normal Ullmann Reaction. Facile Synthesis of SB-214857", Org. Lett., 3 (16), 2001, 2583-2586), the contents of each reference are hereby incorporated by reference in their entirety. For example, the monomer precursors of formula AA-1 can be synthesized as shown in Schemes 8 and 9 below. Other non-limiting methods for synthesizing the precursors of formula AA-1 are shown below. The ubiquitousness of modified amino acids in the literature will lead one of skill in the art to a variety of additional methods to prepare N-modified amino acids.

In an embodiment, in monomer precursor of formula AA-1, variable $R^A$ can be a protected or unprotected side chain of an amino acid. For example, $R^A$ can be the side chain of Alanine, Cysteine, Glycine, Histidine, Isoleucine, Phenylalanine, Serine, Threonine, Tryptophan, Tyrosine, and Valine. In an exemplary embodiment, $R^A$ can be the side chain of Tyrosine where the phenolic hydroxy is protected. For example, the phenolic hydroxy group of Tryptophan can be protected as a methyl ether as shown in the precursor of formula AA-W below.

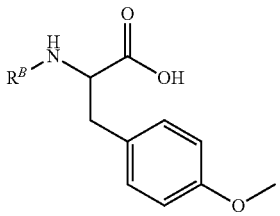

AA-W

In an embodiment, in the monomer precursor of formula AA-1, variable $R^B$ can be an optionally substituted alkyl or aryl substituent. For example, $R^B$ can be branched or unbranched $C_1$-$C_{30}$ alkyl or optionally substituted $C_6$-$C_{30}$ aryl.

In an embodiment, a monomer precursor for formula AA-1 is given by 8-A:

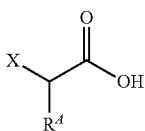

8-A wherein variable X can be Cl, Br, I, tosylate, mesylate, triflate and the like.

Synthetic Schemes: N-Alkyl Monomer Precursors
Scheme 8 Route 1

In an embodiment, a method of introducing the N substituent $R^B$ of monomer precursor AA-1 via a substitution reaction, wherein $R^A$ and $R^B$ is defined as above, and X can be Cl, Br, tosylate, or mesylate defined as above, can be accomplished as shown in Scheme 8 route 1. For example, in compound 8-A the variable X is a good leaving group and can be substituted with the appropriate aryl or alkyl amine (8-B) to afford monomer precursor AA-1 as described in U.S. Pat. No. 3,598,859, which is hereby incorporated by reference in its entirety. Additionally, suitable ester derivatives of 8-A can be used with this method.

Scheme 8
Route 1

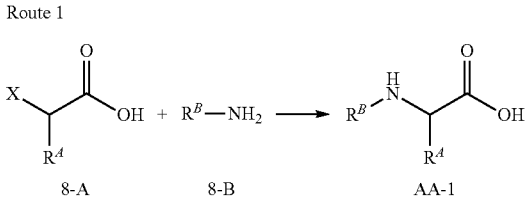

8-A    8-B         AA-1

In some embodiments, coupling of 8-A with a primary, aryl, or heteroarylamine of the formula 8-B under appropriate conditions can provide AA-1. This reaction is described by, for example, U.S. Pat. No. 3,598,859. In an embodiment, the reaction proceeds by combining approximately stoichiometric equivalents of 8-A, wherein X is Cl, Br, or I, with 8-B in a suitable inert diluent such as water, dimethylsulfoxide (DMSO), or the like. The reaction employs an excess of a suitable base such as sodium bicarbonate, sodium hydroxide, etc. to scavenge the acid generated by the reaction. The reaction is preferably conducted at from about 25° C. to about 100° C. until reaction completion which typically occurs within 1 to about 24 hours. Upon reaction completion, AA-1 can be isolated by conventional methods, such as, precipitation, chromatography, filtration and the like.

Scheme 8 Route 2

In one embodiment, a method of introducing the N substituent $R^B$ of monomer precursor AA-1 can be accomplished via a reductive amination reaction, as shown in Scheme 8 route 2, wherein $R^A$, $R^B$, and X are define as above. The α-ketoester 8-C can be treated with the appropriate aryl or alkyl amine (8-B) under reductive amination conditions to afford AA-1 as described in U.S. Pat. No. 3,598,859.

Scheme 8
Route 2

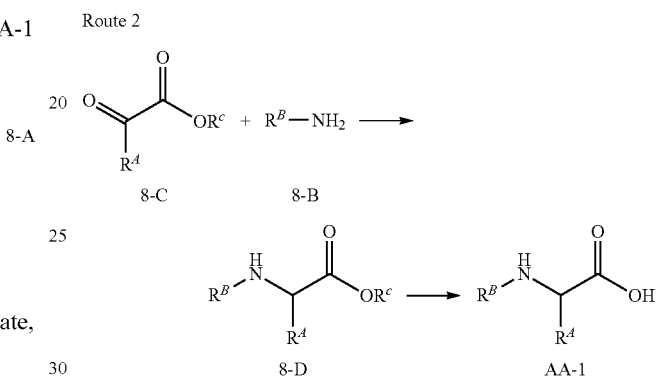

For example, in a exemplary embodiment, approximately stoichiometric amounts of an α-ketoester of formula 8-C and an alkyl or aryl amine of the formula 8-B can be combined in a solvent such as methanol, ethanol and the like and reacted under conditions which provide for imine formation (not shown). The in situ formed imine can be then reduced under conventional conditions by a suitable reducing agent, such as sodium cyanoborohydride, $H_2$/palladium on carbon and the like to form the N-aryl or N-alkyl amino acid ester 8-D. In a typical embodiment, the reducing agent is $H_2$/palladium on carbon which is incorporated into the initial reaction medium which permits imine reduction in situ in a one pot procedure to provide for the N-aryl or N-alkyl amino acid ester 8-D. Subsequent hydrolysis of ester 8-D can afford the monomer precursor AA-1. For example, the ester can be hydrolyzed using wet basic methanol.

Scheme 8 Route 3

In one embodiment, a method of introducing the N substituent $R^B$ of monomer precursor AA-1 can be accomplished via an alkylation reaction of a compound of the formula 8-E and subsequent transformation as shown in Scheme 8 route 3. In some embodiments, $R^A$ and X are define as above, $R^B$ can be branched or unbranched $C_1$-$C_{30}$ alkyl or optionally substituted $C_6$-$C_{30}$ aryl, $R^F$ can be H, $C_1$-$C_6$ alkyl or aryl($CH_2$)—, and $R^E$ can be selected from the group consisting of $CF_3C$(O)—, Cbz—(Carbobenzyloxy), Boc—(tert-Butoxycarbonyl), tosyl—(toluenesulfonyl) or Nosyl—(2-nitrobenzenesulfonyl or 2-nitrobenzenesulfonyl) group, 2,4-dinitrobenzenesulfonyl, and the like. The N-substituted compound of formula 8-E can be treated with an alkylating agent (8-B) under the appropriate conditions to afford 8-G, and the subsequent transformation of 8-G can afford monomer precursor AA-1, as shown below.

Scheme 8

Route 3

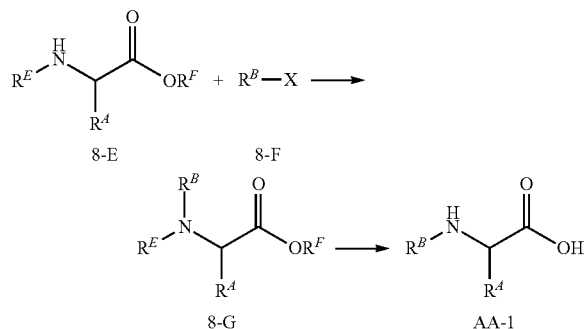

For example, in an exemplary embodiment, Aurelio et al. discloses methods of preparing N-methyl amino acids, these methods can be generally used to prepare additional N-substituted amino acids, such as N-methyl, N-ethyl, N-benzyl and the like.

In an embodiment, treatment of 8-E, wherein $R^E$ is Cbz- or Boc-; $R^F$ is H; and $R^A$ is Me or —CH$_2$Phenyl, with methyl iodide in the presence of Ag$_2$O in DMF affords 8-E, wherein $R^B$ is methyl and $R^F$ is methyl. Subsequent hydrolysis of the methyl ester and removal of the carbamate type protecting group affords the N-methyl amino acid AA-1. This method can be modified to use ethyl iodide in place of methyl iodide to afford the N-ethyl amino acids of formula AA-1. Additionally, this method can be applied to polymers following the procedure of Das et al. (Das, et al., "N-methylation of N-acyl oligopeptides", *Biochem. Biophys. Res. Commun.* 1967,29, 211), the contents of which are hereby incorporated by reference, to afford N-methyl polymers.

In one embodiment, treatment of 8-E, wherein $R^E$ is Cbz- or Boc-; $R^F$ is H; and $R^A$ is Me or —CH$_2$Phenyl with sodium hydride followed by addition of methyl iodide in DMF/THF at 80° C. for 24 h affords 8-E, wherein $R^B$ is methyl and $R^F$ is methyl. Subsequent hydrolysis of the methyl ester with sodium hydroxide in methanol/THF and then removal of the carbamate type protecting group affords the N-methyl amino acid AA-1. This method can be modified to use ethyl iodide in place of methyl iodide to afford the N-ethyl amino acids of formula AA-1. In another embodiment this same procedure can be used to alkylate 8-E wherein $R^F$ is methyl.

In an embodiment, following the procedure of Belagali et al. (Belagali et al. "A Highly Efficient Method of N-Methylation For The Amino-Acid Derivatives", Indian J. Chem. Sect. B, 1995, 34(1), 45), the contents of which are hereby incorporated by reference in their entirety, treatment of 8-E, wherein $R^E$ is Boc-; $R^F$ is H; and $R^A$ is Me or —CH$_2$PhenylOH, with sodium hexamethyldisilazane in THF followed by addition of methyl iodide affords 8-E, wherein $R^B$ is methyl and $R^F$ is methyl. Subsequent hydrolysis of the methyl ester and then removal of the carbamate type protecting group affords the N-methyl amino acid AA-1. This method can be modified to use ethyl iodide in place of methyl iodide to afford the N-ethyl amino acids of formula AA-1. In another embodiment this same procedure can be used to alkylate 8-E wherein $R^F$ is methyl.

In an embodiment, following the procedure of Fukuyama et al., treatment of 8-E, wherein $R^E$ is Nosyl; $R^F$ is Methyl; and $R^A$ is —CH$_2$Phenyl, with K$_2$CO$_3$ in DMF followed by addition of $R^B$—X, wherein $R^B$—X is propyl iodide, affords 8-E, wherein $R^B$ is propyl and $R^F$ is methyl. Subsequent hydrolysis of the methyl ester and then removal of the carbamate type protecting group can afford the N-propyl amino acid AA-1. This method can be modified to use ethyl iodide in place of propyl iodide to afford the N-ethyl amino acids of formula AA-1.

Scheme 8 Route 4

In a typical embodiment, following the procedure of Fukuyama et al., a DMF solution of the amino acid ester of the formula (8-EA) can be treated with ethyl bromide in the presence of K$_2$CO$_3$ to afford 8-GA. Subsequently, the 2,4-dinitrobenzenesulfonyl group can be removed and the ester group can be hydrolyzed to afford AA-1A. For example, the 2,4-dinitrobenzenesulfonyl group of can be removed by treatment of 8-GA with thiophenol and K$_2$CO$_3$ in DMF followed hydrolysis of the methyl ester with NaOH in methanol/THF to afford AA-1A. The N-substituted β-amino acid (AA-1A) can be converted to the N-substituted β-amino ester by methods known to one of skill in the art. For example, the N-substituted β-amino acid can be treated with HCl in a solvent such as ethanol or methanol to afford the corresponding ethyl or methyl N-aryl β-amino esters.

Scheme 8

Route 4

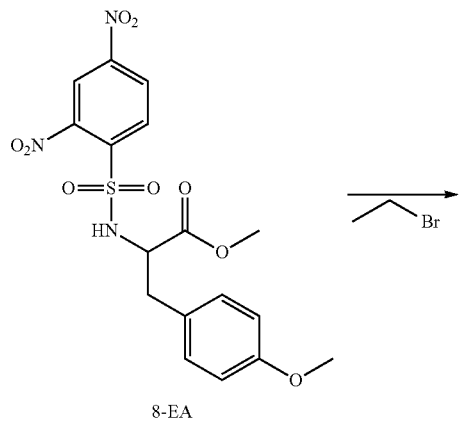

8-EA

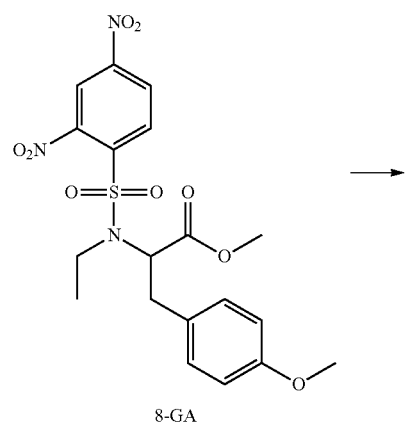

8-GA

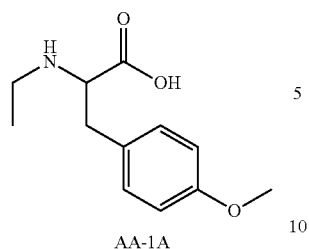

AA-1A

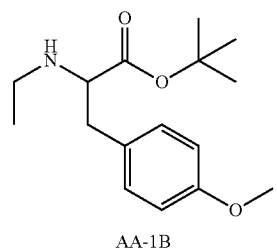

AA-1B

Scheme 8 Route 5

Alternatively, in an exemplary embodiment, a DMF solution of the tert-butyl amino acid ester of the formula (8-EB) can be treated with ethyl bromide in the presence of $K_2CO_3$ to afford 8-GB. Subsequently, the 2,4-dinitrobenzenesulfonyl group can be removed to afford the tert-butyl ester AA-1B. For example, the 2,4-dinitrobenzenesulfonyl group of can be removed by treatment of 8-GB with thiophenol and $K_2CO_3$ in DMF to afford AA-1B.

N-Aryl Monomer Precursors

Scheme 9

In one embodiment, monomer precursor AA-1 can be synthesized, wherein $R^B$ is an aryl group, such as and X is chloride, bromide, or iodide as shown in Scheme 9. For example, the monomer precursor of formula AA-1 can be synthesized by an Ullmann reaction, such as the procedure of Ma et al.

Scheme 9

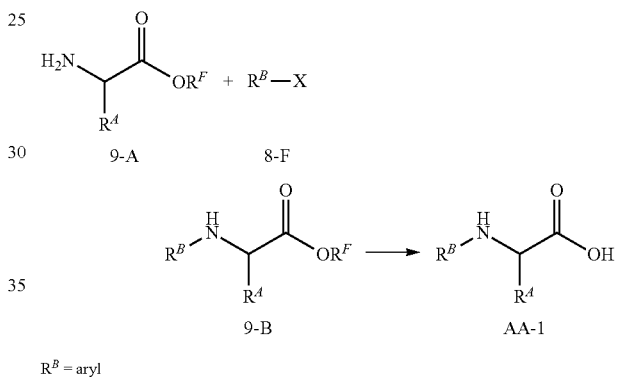

$R^B$ = aryl

In an exemplary embodiment, the amino ester 9-A can be converted to 9-B, as shown in Scheme 9. For example in the presence of phenyl iodide, CuI and $K_2CO_3$ in DMF at 100° C. In one embodiment, the amino ester 9-C can be treated with phenyl iodide (8-F), CuI and $K_2CO_3$ in DMF at 100° C. to afford 9-D, as shown in Scheme 9-A. The N-aryl β-amino acid (9-D) can be converted to the N-aryl β-amino ester by methods known to one of skill in the art. For example, the N-aryl β-amino acid can be treated with HCl in a solvent such as ethanol or methanol to afford the corresponding ethyl or methyl N-aryl β-amino esters.

Scheme 8

Route 5

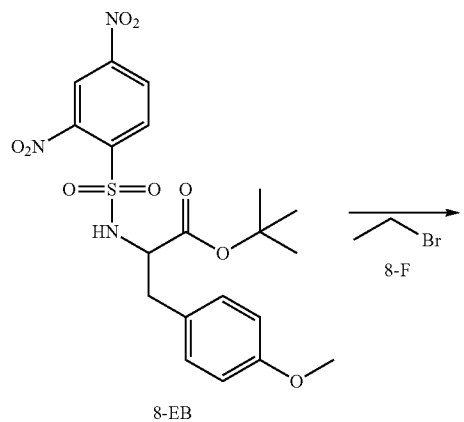

8-EB

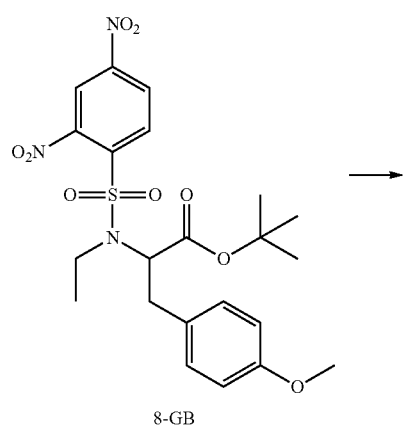

8-GB

Scheme 9-A

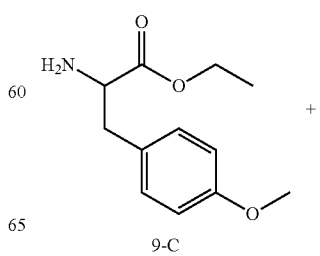

9-C

-continued

8-F → 9-D

In these synthetic methods, the starting materials can contain a chiral center (e.g., alanine) and, when a racemic starting material is employed, the resulting product is a mixture of diastereomers or R,S enantiomers. Alternatively, a chiral isomer of the starting material can be employed and, if the reaction protocol employed does not racemize this starting material, a chiral product is obtained. Such reaction protocols can involve inversion of the chiral center during synthesis.

Accordingly, unless otherwise indicated, the products of this invention are a mixture of diastereomers (if two or more chiral centers are present) or R,S enantiomers (if only one chiral center is present). Preferably, however, when a chiral product is desired, the chiral product corresponds to the L-amino acid derivative. Alternatively, chiral products can be obtained via purification techniques which separates diastereomers or enantiomers from a R,S mixture to provide for one or the other stereoisomer. Such techniques are well known in the art.

Polymers according to the present invention contain a plurality of monomeric repeating units containing an amide group, wherein the amide groups are N-substituted, and the N-substituents and degree of N-substitution are effective to render the polymer processable by a desired processing method. Preferably, the minimum amount of N-substituted monomer is used. This can range from one to three mole percent to render a non-soluble polymer soluble in a given solvent to up to about 25 mole percent to make the same polymer injection moldable. This can be readily determined by one of ordinary skill in the art without undue experimentation.

N-alkyl substituents with one to six carbon atoms are preferred, with N-methyl substituents being more preferred.

The monomer compounds are then polymerized to form tissue compatible bioerodable polymers for medical uses. The diphenol monomers can be used in any conventional polymerization process using diphenol monomers, including those processes that synthesize polymers traditionally considered hydrolytically stable and non-biodegradable.

This includes polyesters, polycarbonates, polyiminocarbonates, polyarylates, polyurethanes, polyphosphazine polyphosphonates and polyethers, as well as random block copolymers of these polymers with poly(alkylene oxides) as described in U.S. Pat. No. 5,658,995, the disclosure of which is incorporated herein by reference.

It is also understood that the presentation of the various polymer formulae that polymer structures represented may include homopolymers and heteropolymers, which include stereoisomers. Homopolymer is used herein to designate a polymer comprised of all the same type of monomers. Heteropolymer is used herein to designate a polymer comprised of two or more different types of monomer, which is also called a co-polymer. A heteropolymer or co-polymer may be of a kind known as block, random and alternating. Further with respect to the presentation of the various polymer formulae, products according to embodiments of the present invention may be comprised of a homopolymer, heteropolymer and/or a blend of such polymers.

Polyiminocarbonates are synthesized from dihydroxy and diphenol monomers via one of the appropriate methods disclosed by U.S. Pat. No. 4,980,449, the disclosure of which is incorporated by reference. According to one method, part of the dihydroxy or diphenol compound is converted to the appropriate dicyanate, then, equimolar quantities of the dihydroxy or diphenol compound and the dicyanate are polymerized in the presence of a strong base catalyst such as a metal alkoxide or metal hydroxide.

The monomers compounds of Formula I may also be reacted with phosgene to form polycarbonates with —O—C(=O)—O— linkages. The method is essentially the conventional method for polymerizing diols into polycarbonates. Suitable processes, associated catalysts and solvents are known in the art and are taught in Schnell, Chemistry and Physics of Polycarbonates, (Interscience, New York 1964), the teachings of which are also incorporated herein by reference.

Other methods adaptable for use to prepare polycarbonate polymers of the present invention are disclosed in U.S. Pat. Nos. 6,120,491, and 6,475,477 the disclosures of which are incorporated herein by reference. Polycarbonates may also be prepared by dissolving the Formula I monomer in methylene chloride containing 0.1M pyridine or triethylamine. A solution of phosgene in toluene at a concentration between about 10 and about 25 wt %, and preferably about 20 wt %, is added at a constant rate, typically over about two hours, using a syringe pump or other means. The reaction mixture is quenched by stirring with tetrahydrofuran (THF) and water, after which the polymer is isolated by precipitation with isopropanol (IPA). Residual pyridine (if used) is then removed by agitation of a THF polymer solution with a strongly acidic resin, such as AMBERLYST 15.

The monomer compounds of formula IV may also be directly reacted with aliphatic or aromatic dicarboxylic acids in the carbodiimide mediated process disclosed by U.S. Pat. No. 5,216,115 using 4-(dimethylamino) pyridinium-p-toluene sulfonate (DPTS) as a catalyst to form the aliphatic or aromatic poly(ester amides). The disclosure of U.S. Pat. No. 5,216,115 is incorporated by reference. Dicarboxylic acids according to one embodiment of the present invention have the structure of Formula V:

HOOC—R$_5$—COOH     (V)

in which, for the aliphatic copolymers, R$_5$ is selected from saturated and unsaturated, substituted and unsubstituted alkyl groups containing up to 18 carbon atoms, and preferably from 2 to 12 carbon atoms, and optionally may also include up to eight N, O, P or S atoms. For the aromatic copolymers, R$_3$ is selected from aryl and alkylaryl groups containing up to 24 carbon atoms and preferably from 13 to 20 carbon atoms, and optionally may also include up to eight N, O, P or S atoms. The N-heteroatoms may be N-substituted to reduce polymer T$_g$ and melt viscosity.

The process forms polymers with —O—C(=O)—R$_5$—C(=O)—O— linkages. R$_5$ may be selected so that the dicarboxylic acids employed as the starting materials are either important naturally-occurring metabolites or highly biocompatible compounds. Aliphatic dicarboxylic acid starting materials therefore include the intermediate dicarboxylic acids of the cellular respiration pathway known as the Krebs Cycle. The dicarboxylic acids include α-ketoglutaric acid, succinic acid, fumaric acid and oxaloacetic acid ($R_5$ of formula III is —$CH_2$—$CH_2$—C(=O)—, —$CH_2$—$CH_2$—, —CH=CH— and —$CH_2$—C(=O)—, respectively).

Another naturally-occurring aliphatic dicarboxylic acid is adipic acid ($R_5$ is (—$CH_2$—)$_4$), found in beet juice. Still yet another biocompatible aliphatic dicarboxylic acid is sebacic acid ($R_5$ is (—$CH_2$—)$_8$), which has been studied extensively and has been found to be nontoxic as part of the clinical evaluation of poly(bis(p-carboxy-phenoxy)propane-co-sebacic acid anhydride) by Laurencin et al., J. Biomed. Mater. Res., 24, 1463-81 (1990).

Other biocompatible aliphatic dicarboxylic acids include oxalic acid ($R_5$ is a bond), malonic acid ($R_5$ is —$CH_2$—), glutaric acid ($R_5$ is (—$CH_2$—)$_3$), pimelic acid ($R_5$ is (—$CH_2$—)$_5$), suberic acid ($R_5$ is (—$CH_2$—)$_6$) and azelaic acid ($R_5$ is (—$CH_2$—)$_7$). $R_5$ can thus represent (—$CH_2$—)$_Q$, wherein Q is between 0 and 8, inclusive. Among the suitable aromatic dicarboxylic acids are terephthalic acid, isophthalic acid and bis(p-carboxy-phenoxy) alkanes such as bis(p-carboxy-phenoxy) propane.

$R_5$ can also have the structure of formula VI:

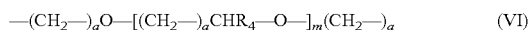

$$-(CH_2-)_aO-[(CH_2-)_aCHR_4-O-]_m(CH_2-)_a \quad (VI)$$

wherein a is from 1 to 3, inclusive, m is from 1 to 500,000, inclusive, and $R_4$ is hydrogen or a lower alkyl group containing from one to four carbon atoms. $R_4$ is preferably hydrogen, a is preferably 1, and m is preferably between about 10 and about 100, and more preferably between about 10 and about 50.

The diacids of formula VI are formed by the oxidation of poly(alkylene oxides) according to well-known methods. One example of such a compound is biscarboxymethyl poly(ethylene glycol), which is commercially available.

$R_5$ can also have the structure of formula VII:

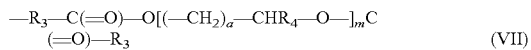

$$-R_3-C(=O)-O[(-CH_2)_a-CHR_4-O-]_mC(=O)-R_3 \quad (VII)$$

wherein a, m and $R_4$ and the preferred species thereof are the same as described above with respect to formula VI. $R_3$ is selected from a bond or straight and branched alkyl and alkylaryl groups containing up to 18 carbon atoms.

The dicarboxylic acids of formula VII are poly(alkylene oxides) bis-functionalized with dicarboxylic acids having the structure of formula V wherein $R_5$ is the same as described above for formula V and preferably contains up to 12 carbon atoms.

The poly(alkylene oxides) of formula VII that are bis-functionalized with dicarboxylic acid are prepared by the reaction of a non-functionalized poly(alkylene oxide) with an excess of either the dicarboxylic acid (mediated by a coupling agent such as dicyclohexyl carbodiimide), the anhydride (e.g. succinic anhydride) in the presence of pyridine or triethylamine, or a dicarboxylic acid chloride (e.g. adipoyl chloride) in the presence of an acid acceptor like triethylamine.

Polymers prepared from the formula IV monomeric starting materials of the present invention with at least one bromine- or iodine-substituted aromatic ring are radio-opaque, such as the polymers prepared from radiopaque diphenol compounds prepared according to the disclosure of U.S. Pat. No. 6,475,477, as well as he disclosure of co-pending and commonly-owned U.S. patent application Ser. No. 10/592,202, the disclosures of both of which are incorporated herein by reference. The iodinated and brominated diphenol monomers of the present invention can also be employed as radio-opacifying, biocompatible non-toxic additives for other polymeric biomaterials.

Bromine and iodine substituted aromatic monomers of the present invention are prepared by well-known iodination and bromination techniques that can be readily employed by those of ordinary skill in the art guided by the above referenced granted patent and pending application (now published) without undue experimentation. The halogenated aromatic compounds from which the halogenated aromatic monomers the present invention are prepared undergo ortho-directed halogenation. The term, "ortho-directed", is used herein to designate orientation of the halogen atom(s) relative to the phenoxy alcohol group.

Random or block copolymers of the formula I polymers of the present invention with a poly(alkylene oxide) may be prepared according to the method disclosed in U.S. Pat. No. 5,658,995, the disclosure of which is also incorporated by reference. The poly(alkylene oxide) is preferably a poly(ethylene glycol) block/unit typically having a molecular weight of less than about 10,000 per unit. More typically, the poly(ethylene glycol) block/unit has a molecular weight less than about 4000 per unit. The molecular weight is preferably between about 1000 and about 2000 per unit.

The molar fraction of poly(ethylene glycol) units in block copolymers may range from grater than zero to less than 1, and is typically greater than zero up to about 0.5, inclusive. More preferably, the molar fraction is less than about 0.25 and yet more preferably, less than about 0.1. In a more preferred variations, the molar fraction may vary from greater than about 0.001 to about 0.08, and most preferably, between about 0.025 and about 0.035.

Unless otherwise indicated, the molar fractions reported herein are based on the total molar amount of poly(alkylene glycol) and non-glycol units in the polymers Applicants have also recognized that the polymer glass transition temperature increases as the degree of halogenation and the molar fraction of free carboxylic acid units increases. Higher weight percentages of poly(alkylene oxide) are typically used in polymers with higher levels of iodination and/or with higher molar fractions of free carboxylic acid units to maintain the polymer glass transition temperature within a desired range for the end use application. N-alkylation provides an alternative means for lowering the polymer glass transition temperature so that the amount of poly(alkylene oxide) may be lowered or eliminated without adversely affecting the polymer melt properties. The present invention thus places more tools at the disposal of the polymer chemist for fine-tuning the physico-mechanical properties of the inventive polymers.

The formula I polymers having weight-average molecular weights above about 20,000, and preferably above about 80,000, calculated from gel permeation chromatography (GPC) relative to polystyrene standards using tetrahydrofuran (THF) as the eluent without further correction.

The polymers of the present invention are defined as including polymers polymerized from formula IV monomers having pendent free carboxylic acid groups ($R_8$=OH). However, it is not possible to polymerize polymers having pendent free carboxylic acid groups from corresponding monomers with pendent free carboxylic acid groups without cross-reaction of the free carboxylic acid group with the co-monomer. Accordingly, polymers in accordance with the present invention having pendent free carboxylic acid groups are prepared from homopolymers and copolymers of benzyl and tert-butyl ester monomers of the present invention having the structure of formula IV in which $R_8$ is a benzyl or tert-butyl group.

The benzyl ester homopolymers and copolymers may be converted to corresponding free carboxylic acid homopolymers and copolymers through the selective removal of the benzyl groups by the palladium catalyzed hydrogenolysis method disclosed by co-pending and commonly owned U.S. Pat. No. 6,120,491, the disclosure of which is incorporated herein by reference.

The tert-butyl ester homopolymers and copolymers may be converted to corresponding free carboxylic acid homopolymers and copolymers through the selective removal of the tert-butyl groups by the acidolyis method disclosed by the above-referenced U.S. patent application Ser. No. 10/592, 202, also incorporated herein by reference.

The catalytic hydrogenolysis or acidolysis is necessary because the lability of the polymer backbone prevents the employment of harsher hydrolysis techniques.

Applicants have recognized that the molar fraction of free carboxylic acid units in the polymers of the present invention can be adjusted according to the present invention to likewise adjust the degradation/resorbability of devices made from such polymers. For example, applicants have recognized that while poly(DTE-co-35 mol % DT carbonate), (a tyrosine-derived polycarbonate comprising about 35% free carboxylic acid units) is 90% resorbed in about 15 days, polycarbonates with lower amounts of free carboxylic acid will have desirably longer lifetimes in the body. Furthermore, by otherwise adjusting the amount of free carboxylic acid in the polymers across the range of preferred molar fraction, the resulting polymers can be adapted for use in various applications requiring different device lifetimes. In general, the higher the molar fraction of free carboxylic acid units, the shorter the lifetime of the device in the body and more suitable such devices are for applications wherein shorter lifetimes are required. In certain embodiments where lifetimes of 6 months or more are required, polymers of the presently preferred ranges of free carboxylic acid units tend to be desirable.

The present invention also includes N-substituted versions of the monomers and polymers of Pacetti, U.S. Pat. Application Pub. No. 2006-0115449, incorporated by reference herein in its entirety, prepared according to the N-substitution methods disclosed herein.

After polymerization, appropriate work up of the polymers in accordance with preferred embodiments of the present invention may be achieved by any of a variety of known methods commonly employed in the field of synthetic polymers to produce a variety of useful articles with valuable physical and chemical properties, all derived from tissue compatible monomers. The useful articles can be shaped by conventional polymer-forming techniques such as extrusion, compression molding, injection molding, solvent casting, spin casting, wet spinning, combinations of two or more thereof, and the like. Shaped articles prepared from the polymers are useful, inter alia, as degradable biomaterials for medical implant applications. Such applications include the use of shaped articles as vascular grafts and stents.

Stent fabrication processes may further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms. In certain other embodiments, the polymers are formed into coatings on the surface of an implantable device, particularly a stent, made either of a polymer of the present invention or another material, such as metal. Such coatings may be formed on stents via techniques such as dipping, spray coating, combinations thereof, and the like. Further, stents may be comprised of at least one fiber material, curable material, laminated material, and/or woven material. Details of stent products and fabrication in which the polymers of the present invention may be employed are disclosed in co-pending and commonly-owned U.S. patent application Ser. No. 10/952,202 filed Sep. 27, 2004, the disclosure of which is incorporated by reference. Stents are preferably fabricated from the radiopaque polymers of the present invention, to permit fluoroscopic positioning of the device.

The highly beneficial combination of properties associated with the preferred polymers in accordance with embodiments of the present invention are well-suited for use in producing a variety of medical devices besides stents, especially implantable medical devices that are preferably radiopaque, biocompatible, and have various times of bioresorption. For example, applicants have recognized that, in certain embodiments, the polymers are suitable for use in producing implantable devices for orthopedics, tissue engineering, dental applications, wound closure, gastric lap bands, drug delivery, cancer treatment, other cardiovascular applications, non-cardiovascular stents such as biliary, esophagus, vaginal, lung-trachea/bronchus, and the like. In addition, the polymers are suitable for use in producing implantable, radiopaque discs, plugs, and other devices used to track regions of tissue removal, for example, in the removal of cancerous tissue and organ removal, as well as, staples and clips suitable for use in wound closure, attaching tissue to bone and/or cartilage, stopping bleeding (homeostasis), tubal ligation, surgical adhesion prevention, and the like. Applicants have also recognized that the polymers of the present invention are well-suited for use in producing a variety of coatings for medical devices, especially implantable medical devices.

Furthermore, in some preferred embodiments, the present polymers may be advantageously used in making various orthopedic devices including, for example, radiopaque biodegradable screws (interference screws), radiopaque biodegradable suture anchors, and the like for use in applications including the correction, prevention, reconstruction, and repair of the anterior cruciate ligament (ACL), the rotator cuff/rotator cup, and other skeletal deformities.

Other devices, which can be advantageously formed from the polymers of the present invention, include devices for use in tissue engineering. Examples of suitable devices include tissue engineering scaffolds and grafts (such as vascular grafts, grafts or implants used in nerve regeneration). The present polymers may also be used to form a variety of devices effective for use in closing internal wounds. For example, biodegradable sutures, clips, staples, barbed or mesh sutures, implantable organ supports, and the like, for use in various surgery, cosmetic applications, and cardiac wound closures can be formed.

Various devices finding use in dental applications may advantageously be formed according to preferred aspects of the present invention. For example, devices for guided tissue regeneration, alveolar ridge replacement for denture wearers, and devices for the regeneration of maxilla-facial bones may benefit from being radiopaque so that the surgeon/dentist can ascertain the placement and continuous function of such implants by simple X-ray imaging.

The present polymers are also useful in the production of gastric lap bands for use in the treatment of obesity. The production of radiopaque lap bands allows for more effective monitoring of the devices in the human body, and more effective treatment of obesity.

In addition to intravascular stents and non-cardiovascular stents, the present polymers are useful in a number of other cardiovascular and vascular devices. For example, valves, chordae tendinea replacements, annuloplasty rings, leaflet repair patches, vascular grafts, vascular tubes, patches for septal defects, arterial and venous access closure devices (plugs), and the like can be formed for use in replacement repair of heart valves, tubes, and the like. In addition, portions of an artificial heart, such as the rough surface/fibroid layer (bellow pumps) may be formed from the polymers of the instant invention.

The polymers of the present invention are also useful in the production of bioresorbable, inherently radiopaque polymeric embolotherapy products for the temporary and therapeutic restriction or blocking of blood supply to treat tumors and vascular malformations, e.g., uterine fibroids, tumors (i.e., chemoembolization), hemorrhage (e.g., during trauma with bleeding) and arteriovenous malformations, fistulas and aneurysms delivered by means of catheter or syringe. Details of embolotherapy products and methods of fabrication in which the polymers of the present invention may be employed are disclosed in co-pending and commonly-owned U.S. patent application Ser. No. 10/952,274 filed Sep. 27, 2004, the disclosure of which is incorporated by reference. Embolotherapy treatment method are by their very nature local rather than systemic and the products are preferably fabricated from the radiopaque polymers of the present invention, to permit fluoroscopic monitoring of delivery and treatment.

The present polymers are further useful in the production of a wide variety of therapeutic agent delivery devices. Such devices may be adapted for use with a variety of therapeutics including, for example, pharmaceuticals (i.e., drugs) and/or biological agents as previously defined and including biomolecules, genetic material, and processed biologic materials, and the like. Any number of transport systems capable of delivering therapeutics to the body can be made, including devices for therapeutics delivery in the treatment of cancer, intravascular problems, dental problems, obesity, infection, and the like.

In certain embodiments, any of the aforementioned devices described herein can be adapted for use as a therapeutic delivery device (in addition to any other functionality thereof). Controlled therapeutic delivery systems may be prepared, in which a therapeutic agent, such as a biologically or pharmaceutically active and/or passive agent, is physically embedded or dispersed within a polymeric matrix or physically admixed with a polymer of the present invention. Controlled therapeutic agent delivery systems may also be prepared by direct application of the therapeutic agent to the surface of an implantable medical device such as a bioresorbable stent device (comprised of at least one of the present polymers) without the use of these polymers as a coating, or by use of other polymers or substances for the coating.

The $Q^1$ pendant groups of the polymers of the present invention may also be derivatized by the covalent attachment of a therapeutic agent. Depending upon whether $Q^1$ defines a free carboxylic acid, a carboxylic acid amide, a hydroxyl group, or the like, and depending upon the moieties present on the underivaitized therapeutic agent, the covalent bond may be an amide bond or an ester bond. Typically, the therapeutic agent is derivatized at a primary or secondary amine, hydroxyl, ketone, aldehyde or carboxylic acid group. Chemical attachment procedures are described by U.S. Pat. Nos. 5,219,564 and 5,660,822; Nathan et al., Bio. Cong. Chem., 4, 54-62 (1993) and Nathan, Macromolecules, 25, 4476 (1992), the disclosures of which are incorporated by reference. The therapeutic agent may first be covalently attached to a monomer, which is then polymerized, or the polymerization may be performed first, followed by covalent attachment of the therapeutic agent.

Hydrolytically stable conjugates are utilized when the therapeutic agent is active in conjugated form. Hydrolyzable conjugates are utilized when the therapeutic agent is inactive in conjugated form.

Therapeutic agent delivery compounds may also be formed by physically blending the therapeutic agent to be delivered with the polymers of the present invention using conventional techniques well-known to those of ordinary skill in the art. For this therapeutic agent delivery embodiment, it is not essential that the polymer have pendent groups for covalent attachment of the therapeutic agent.

The polymer compositions of the present invention containing therapeutic agents, regard-less of whether they are in the form of polymer conjugates or physical admixtures of polymer and therapeutic agent, are suitable for applications where localized delivery is desired, as well as in situations where a systemic delivery is desired. The polymer conjugates and physical admixtures may be implanted in the body of a patient in need thereof, by procedures that are essentially conventional and well-known to those of ordinary skill in the art.

Implantable medical devices may thus be fabricated that also serve to deliver a therapeutic agent to the site of implantation by being fabricated from or coated with the therapeutic agent delivery system of the present invention in which a polymer of the present invention has a therapeutic agent physically admixed therein or covalently bonded thereto, such as a drug-eluting stent. Embolotherapeutic particles may also be fabricated for delivery of a therapeutic agent.

Examples of biologically or pharmaceutically active therapeutic agents that may by covalently attached to the polymers of the present invention include acyclovir, cephradine, malphalen, procaine, ephedrine, adriamycin, daunomycin, plumbagin, atropine, quinine, digoxin, quinidine, biologically active peptides, chlorin e.sub.6, cephradine, cephalothin, proline and proline analogs such as cis-hydroxy-L-proline, malphalen, penicillin V, aspirin and other non-steroidal anti-inflammatories, nicotinic acid, chemodeoxycholic acid, chlorambucil, anti-tumor and anti-proliferative agents, including anti-proliferative agents that prevent restenosis, hormones such as estrogen, and the like. Biologically active compounds, for the purposes of the present invention, are additionally defined as including cell attachment mediators, biologically active ligands, and the like.

The invention described herein also includes various pharmaceutical dosage forms containing the polymer-therapeutic agent combinations of the present invention. The combination may be a bulk matrix for implantation or fine particles for administration by traditional means, in which case the dosage forms include those recognized conventionally, e.g. tablets, capsules, oral liquids and solutions, drops, parenteral solutions and suspensions, emulsions, oral powders, inhalable solutions or powders, aerosols, topical solutions, suspensions, emulsions, creams, lotions, ointments, transdermal liquids and the like.

The dosage forms may include one or more pharmaceutically acceptable carriers. Such materials are non-toxic to the recipients at the dosages and concentrations employed, and include diluents, solubilizers, lubricants, suspending agents, encapsulating materials, penetration enhancers, solvents, emollients, thickeners, dispersants, buffers such as phosphate, citrate, acetate and other organic acid salts, anti-oxidants such as ascorbic acid, preservatives, low molecular weight (less than about 10 residues) peptides such as polyarginine, proteins such as serum albumin, gelatin, or immunoglobulins, other hydrophilic polymers such as poly(vinylpyrrolidinone), amino acids such as glycine, glutamic acid, aspartic acid, or arginine, monosaccharides, disaccharides, and other carbohydrates, including cellulose or its derivatives, glucose, mannose, or dextrines, chelating agents such as EDTA, sugar alcohols such as mannitol or sorbitol, counterions such as sodium and/or nonionic surfactants such as tween, pluronics or PEG.

The therapeutic agents to be incorporated in the polymer conjugates and physical admixtures of this invention may be provided in a physiologically acceptable carrier, excipient stabilizer, etc., and may be provided in sustained release or timed release formulations supplemental to the polymeric formulation prepared in this invention. Liquid carriers and diluents for aqueous dispersions are also suitable for use with the polymer conjugates and physical admixtures.

Subjects in need of treatment, typically mammalian, using the polymer-therapeutic agent combinations of this invention, can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize. The polymer-therapeutic agent combinations of this invention may be prepared for storage under conditions suitable for the preservation of therapeutic agent activity as well as maintaining the integrity of the polymers, and are typically suitable for storage at ambient or refrigerated temperatures.

Aerosol preparations are typically suitable for nasal or oral inhalation, and may be in powder or solution form, in combination with a compressed gas, typically compressed air. Additionally, aerosols may be used topically. In general, topical preparations may be formulated to enable one to apply the appropriate dosage to the affected area once daily, and up to three to four times daily, as appropriate.

Depending upon the particular compound selected, transdermal delivery may be an option, providing a relatively steady delivery of the drug, which is preferred in some circumstances. Transdermal delivery typically involves the use of a compound in solution, with an alcoholic vehicle, optionally a penetration enhancer, such as a surfactant, and other optional ingredients. Matrix and reservoir type transdermal delivery systems are examples of suitable transdermal systems. Transdermal delivery differs from conventional topical treatment in that the dosage form delivers a systemic dose of the therapeutic agent to the patient.

The polymer-drug formulations of this invention may also be administered in the form of liposome delivery systems, such as small unilamellar vesicles, large unilamellar vesicles and multilamellar vesicles. Liposomes may be used in any of the appropriate routes of administration described herein. For example, liposomes may be formulated that can be administered orally, parenterally, transdermally, or via inhalation. Therapeutic agent toxicity could thus be reduced by selective delivery to the affected site. For example, if the therapeutic agent is liposome encapsulated, and is injected intravenously, the liposomes used are taken up by vascular cells and locally high concentrations of the therapeutic agent could be released over time within the blood vessel wall, resulting in improved action of the therapeutic agent. The liposome encapsulated therapeutic agents are preferably administered parenterally, and particularly, by intravenous injection.

Liposomes may be targeted to a particular site for release of the therapeutic agent. This would obviate excessive dosages that are often necessary to provide a therapeutically useful dosage of a therapeutic agent at the site of activity, and consequently, the toxicity and side effects associated with higher dosages.

The therapeutic agents incorporated into the polymers of this invention may desirably further incorporate agents to facilitate their delivery systemically to the desired target, as long as the delivery agent meets the same eligibility criteria as the therapeutic agents described above. The active therapeutic agents to be delivered may in this fashion be incorporated with antibodies, antibody fragments, growth factors, hormones, or other targeting moieties, to which the therapeutic agent molecules are coupled.

The polymer-therapeutic agent combinations of this invention may also be formed into shaped particles, such as valves, stents, tubing, prostheses, and the like.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rate from the formulations of this invention are also varied within the routine skill in the art to determine an advantageous profile, depending on the therapeutic conditions to be treated.

A typical dosage might range from about 0.001 mg/k/g to about 1,000 mg/k/g, preferably from about 0.01 mg/k/g to about 100 mg/k/g, and more preferably from about 0.10 mg/k/g to about 20 mg/k/g. Advantageously, the compounds of this invention may be administered several times daily, and other dosage regimens may also be useful.

In practicing the methods of this invention, the polymer-therapeutic agent combinations may be used alone or in combination with other therapeutic or diagnostic agents. The compounds of this invention can be utilized in vivo, ordinarily in mammals such as primates such as humans, sheep, horses, cattle, pigs, dogs, cats, rats and mice, or in vitro.

One major advantage of using the radiopaque, bioresorbable polymers of the instant invention in therapeutic agent delivery applications is the ease of monitoring the release of a therapeutic agent and the presence of the implantable therapeutic delivery system. Because the radiopacity of the polymeric matrix is due to covalently attached halogen substituents, the level of radiopacity is directly related to the residual amount of the degrading therapeutic agent delivery matrix still present at the implant site at any given time after implantation. In preferred embodiments, the rate of therapeutic release from the degrading therapeutic delivery system will be correlated with the rate of polymer resorption. In such preferred embodiments, the straightforward, quantitative measurement of the residual degree of radio-opacity will provide the attending physician with a way to monitor the level of therapeutic release from the implanted therapeutic delivery system.

The following non-limiting examples set forth herein below illustrate certain aspects of the invention. All parts and percentages are by mole percent unless otherwise noted and all temperatures are in degrees Celsius unless otherwise indicated. All solvents were HPLC grade and all other reagents were of analytical grade and were used as received, unless otherwise indicated.

EXAMPLES

Example 1

N-Alkyl Substitution

In a pressure vessel compound 8-EB is dissolved in DMF with $K_2CO_3$ (2 equiv) at room temperature and then treated with ethyl bromide (1.1 equiv.) dropwise via syringe. The pressure vessel is then sealed and the reaction is heated to 60° C., at 30 min intervals the reaction is allowed to cool to room temperature and the progress is checked by TLC (thin layer chromatography) or LC/MS. The reaction is quenched with water and the aqueous layer is extracted. The organic layer is dried over $Na_2SO_4$, filtered and the solvent removed under reduced pressure to afford 8-GB. The intermediate 8-GB is dissolved in DMF in the presence of excess $K_2CO_3$, then thiophenol is added and the mixture is stirred at room temperature until the completion of the reaction as indicated by TLC. The solid is removed by filtration and the solvent is removed under reduced pressure. The crude mixture is then dissolved in wet methanol/THF in the presence of catalytic NaOH, upon completion of the hydrolysis of the ester the solvent is removed under reduced pressure. The residue was dissolved in water, acidified to pH 5, and extracted with ethyl acetate to afford AA-1B.

Example 2

N-Aryl Substitution

To a solution of phenyl iodide (1 mmol) and β-amino ester (9-C) (1 mmol) in DMF (5 mL) is added potassium carbonate (2.5 mmol), 0.1 mL of water, and CuI (0.1 mmol) under nitrogen. After the mixture is stirred at 100° C. for 48 h under nitrogen atmosphere, the cooled solution is concentrated in vacuo. The residue is dissolved in water, acidified to pH 5, and extracted with ethyl acetate. The combined organic layers are concentrated and purified by chromatography to afford the corresponding N-aryl β-amino acid (9-D).

The N-aryl β-amino acid (9-D) can be converted to the N-aryl β-amino acid by methods known to one of skill in the art. For example, the N-aryl β-amino acid can be treated with HCl in a solvent such as ethanol or methanol to afford the corresponding ethyl or methyl N-aryl β-amino esters.

Example 3

N-Substituted Monomers

Monomer PP-IA:

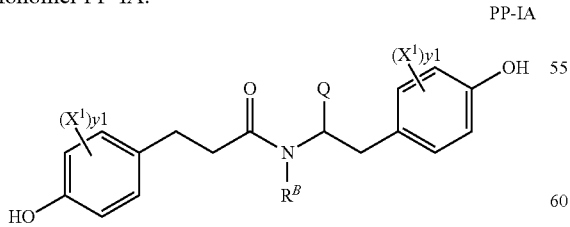

can be synthesized from the monomer precursor of formula AA-1. In a typical embodiment, as shown in Scheme 10, the polymerization precursor 10-C can be synthesized from AA-1B. Iodination of 3-(4-hydroxyphenyl)propionic acid (10-A) affords 3-(4-hydroxy-3,5-diiodophenyl)propanoic acid. Subsequent coupling of 10-B with AA-1B followed by removal of the phenol protecting group afford the polymerization precursor 10-C. For example, treatment of 3-(4-hydroxyphenyl)propionic acid (10-A) with chloroiodide affords 3-(4-hydroxy-3,5-diiodophenyl)propanoic acid (10-B). Coupling of 10-B with AA-1B using N-(3-Dimethylaminopropyl)-N'-ethylcarbodiimide hydrochloride (EDCI) followed by deprotection of the phenol protecting group can afford the polymerization precursor 10-C. The removal of the methyl protecting group can be accomplished using boron tribromide ($BBr_3$) in methylene chloride (DCM). The polymerization precursor 10-C can be converted into polymeric form following the methods disclosed in synthetic scheme 1-6. Additional monomer subunits can be synthesized from monomer precursors of formula AA-1 following the method of Scheme 10 with appropriate modifications readily apparent to one of skill in the art.

Scheme 10

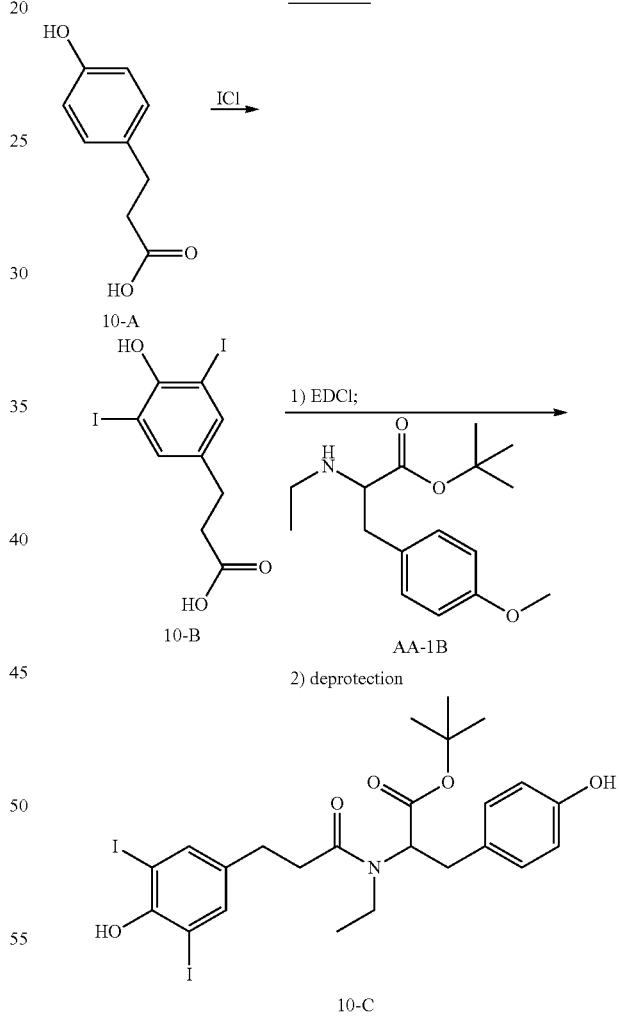

Example 4

Preparation of Di-Iodinated Aromatic Hydroxy Acids

A 2 M solution of KICl2 was prepared using a literature procedure.[1] In a 2 L beaker were stirred place 166.2 g (1.0 mole) of DAT and 800 mL 2-propanol. To the resulting solution was added 158 g (2.0 mole) of pyridine and 1 L (2.0 moles) of 2 M solution of KICl$_2$. After 1 h of stirring 3 L of water was added to the reaction mixture, and the product that precipitated was collected by filtration and washed with water. For further purification the crude product was dissolved in 4 L of water containing 80 g (2.0 mol) of sodium hydroxide and filtered. The filtrate was cooled to room temperature and acidified with acetic acid to a pH of 5.5. The product was isolated by filtration and washed with several portions of water and then dried under vacuum for constant weight which gave 375 g (90% yield) of 3-(3,5-diiodo-4-hydroxyphenyl)propionic acid (I$_2$DAT). Using similar procedures 4-hydroxyphenyl acetic acid and 4-hydroxy benzoic acid were iodinated to the corresponding di-iodinated compounds.

Example 5

Synthesis of I$_2$DAT-NMeTyr-OMe Monomer

A diphenolic monomer was prepared by coupling the 3-(3,5-diiodo-4-hydroxyphenyl)propionic acid (I$_2$DAT) of Example 1 with N-methyl tyrosine methyl ester HCl salt (NMeTM.HCl) (Bache Biosciences, Inc. King of Prussia, Pa.) using 1-(3-dimethylaminopropyl)-3-ethyl carbodiimide hydrochloride (EDC) as the coupling agent. In particular, 1.6 g (3.8 mmol) of I$_2$DAT, 0.99 g (4.02 mmol) of NMeTM.HCl 54 mg (0.40 mmol) of hydroxybenzotriazole and 20 mL of tetrahydrofuran was stirred in a 50 mL round-bottomed flask at 0-5° C. To the flask was then added EDC (0.81 g, 4.2 mmol).

The reaction mixture was stirred at 0 to 5° C. for 1 h and then at room temperature for 3 h. Most of the THF was evaporated off and the reaction mixture was stirred with 50 mL of ethyl acetate and 50 mL 0.2 M HCl. The layers were separated using a separatory funnel. The organic layer was washed with 3×25 mL of 0.2 M HCl, 3×25 mL of 5% sodium bicarbonate solution and 25 mL of 20% NaCl. The organic layer was then concentrated when an oil was obtained. The product was identified as N-methyl I$_2$DTE by $^1$H NMR and elemental analysis. HPLC gave a peak with expected retention time along with a minor byproduct which is normally present even when simple tyrosine esters are used.

Example 6

Polymerization of NMe-I$_2$DTE

The diphenolic monomer NMe-I$_2$DTE of Example 2 was polymerized to form a polycarbonate using the standard phosgenation procedure disclose by U.S. Pat. No. 5,099,060.

Example 7

Synthesis of Monomers of N-Alkyl Tyrosine Esters

Preparation of diphenolic monomers from N-alkyl tyrosine esters is exemplified by the synthesis of N-ethyl I$_2$DTE. In particular, 1.6 g (3.8 mmol) of I$_2$DAT, 1.10 g (4.02 mmol) of N-ethyl tyrosine ethyl ester HCl salt (NEtTE.HCl—prepared by the method disclosed by Aureilo, et al., *Chem. Rev.*, 104, 5823-46 (2004), the entire disclosure of which is incorporated by reference), 54 mg (0.40 mmol) of hydroxybenzotriazole and 20 mL of tetrahydrofuran is stirred in a 50 mL round-bottomed flask at 0-5° C. To the flask is then added EDC (0.81 g, 4.2 mmol). The reaction mixture is stirred at 0 to 5° C. for 1 h and then at room temperature for 3 h. Most of the THF is evaporated off and the reaction mixture is stirred with 50 mL of ethyl acetate and 50 mL 0.2 M HCl. The layers are separated using a separatory funnel. The organic layer is washed with 3×25 mL of 0.2 M HCl, 3×25 mL of 5% sodium bicarbonate solution and 25 mL of 20% NaCl. The organic layer is then concentrated when an oil is obtained. The product is characterized by $^1$H NMR, elemental analysis and HPLC.

Example 8

Thioamide Synthesis and N-Alkylation

In a Schlenck tube are placed diacetyl-I$_2$DTE (693 mg, 1.0 mmol), f$_6$LR (1.13 g, 1.0 mmol), and 20 mL of THF. The Schlenck tube is heated in an oil bath 55° C. for 4 h. To the reaction mixture is then added 10 g of alumina and the solvent was removed by evaporation. The crude product is purified by short column packed with fluorous reverse phase silica. The product is then subjected to hydrolysis with dilute sodium hydroxide followed by acidification to give the I$_2$DTE-thioamide. The compound is then N-methylated according to Example 7.

The description of the preferred embodiments should be taken as illustrating, rather than as limiting, the present invention as defined by the claims. As will be readily appreciated, numerous combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A blood-contacting or tissue-implantable medical device formed from a biocompatible, bioresorbable polymer comprising a plurality of monomeric repeating units containing an amide group, wherein said amide groups comprise N-substituted amide groups and the N-substituents and degree of N-substitution are effective to lower the melt viscosity of said polymer, the solution viscosity of said polymer, or both, compared to the same polymer without N-substitution.

2. The medical device according to claim 1, wherein said N-substituents and degree of N-substitution are effective to reduce the melt viscosity of said polymer, the solution viscosity of said polymer, or both, at least about 5%.

3. The medical device according to claim 1, wherein said N-substituents of said polymer comprise C$_1$-C$_6$ alkyl groups.

4. A biocompatible, bioresorbable polymer comprising one or more recurring units of the formula:

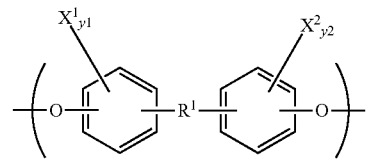

wherein X$^1$ and X$^2$ are each independently selected from Br and I; y1 and y2 are each independently zero or an integer in the range of 1 to 4, and R$^1$ is selected from the group consisting of substituted or unsubstituted, saturated or unsaturated, straight chain or branched aliphatic groups containing up to 48 carbon atoms, substituted or unsubstituted aromatic groups containing up to 48 carbon atoms, and substituted or unsubstituted araliphatic groups containing up to 48 carbon atoms in which the aliphatic portions are straight chain or branched and saturated or unsaturated, and $R^1$ contains from 2 to 8 heteroatoms selected from O, S and N, in which two of the heteroatoms form a polymer backbone amide group, wherein some or all of the recurring units comprise backbone amide groups that are N-substituted with a $C_1$-$C_6$ alkyl group;

wherein the degree of N-substitution is effective to lower the melt viscosity, the solution viscosity, or both, compared to the same polymer without N-substitution; and wherein said polymer has a weight-average molecular weight above about 20,000.

5. A biocompatible, bioresorbable polymer comprising one or more recurring units of the formula:

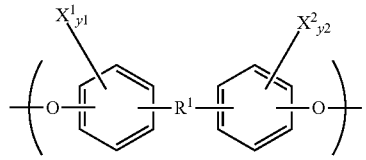

wherein $X^1$ and $X^2$ are each independently selected from Br and I; y1 and y2 are each independently zero or an integer in the range of 1 to 4, and $R^1$ is selected from the group consisting of substituted or unsubstituted, saturated or unsaturated, straight chain or branched aliphatic groups containing up to 48 carbon atoms, substituted or unsubstituted aromatic groups containing up to 48 carbon atoms, and substituted or unsubstituted araliphatic groups containing up to 48 carbon atoms in which the aliphatic portions are straight chain or branched and saturated or unsaturated, and R1 contains from 2 to 8 heteroatoms selected from O, S and N, in which two of the heteroatoms form a polymer backbone amide group;

wherein some or all of the recurring units comprise backbone amide groups that are N-substituted with a $C_1$-$C_6$ alkyl group, wherein said $R^1$ group further comprises poly (alkylene oxide) heteroatoms; and wherein the degree of N-substitution is effective to lower the melt viscosity, the solution viscosity, or both, compared to the same polymer without N-substitution.

6. The polymer of claim 4, wherein $R^1$ contains between about 18 and about 36 carbon atoms.

7. A biocompatible, bioresorbable polymer comprising one or more recurring units of the formula:

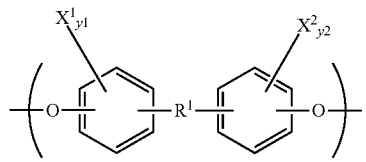

wherein $X^1$ and $X^2$ are each independently selected from Br and I; y1 and y2 are each independently zero or an integer in the range of 1 to 4, and $R^1$ is selected from the group consisting of substituted or unsubstituted, saturated or unsaturated, straight chain or branched aliphatic groups containing up to 48 carbon atoms, substituted or unsubstituted aromatic groups containing up to 48 carbon atoms, and substituted or unsubstituted araliphatic groups containing up to 48 carbon atoms in which the aliphatic portions are straight chain or branched and saturated or unsaturated, and $R^1$ contains from 2 to 8 heteroatoms selected from O, S and N, in which two of the heteroatoms form a polymer backbone amide group;

wherein some or all of the recurring units comprise backbone amide groups that are N-substituted with a $C_1$-$C_6$ alkyl group;

wherein $R^1$ is:

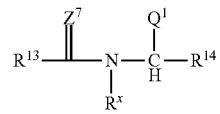

in which $R^{13}$ and $R^{14}$ each independently contain between 0 and 8 carbons atoms, inclusive, and are independently selected from $(-CHR^1)_e-CH=CH-(CHR^1-)_e$ and $(-CHR^1)_f(-CHNQ^2)_g(-CHR^1)_f$, wherein $R^1$ is H or lower alkyl, each e independently ranges between 0 and 6, inclusive, each f independently ranges between 0 and 8, inclusive and g is 0 or 1; $Z^7$ is O or S; $R^x$ is a $C_1$-$C_6$ alkyl group; $Q^1$ is $C(=Z^5)-R^8$, wherein $Z^5$ is O or S; $Q^2$ is $-N(R^x)_2$ or $-N(R^xQ^1)$ and $R^8$ is selected from the group consisting of H, OH, a therapeutically active moiety, a poly(alkylene oxide), $-X_3-C_i$-$C_{18}$ alkyl, $-X_3$-alkenyl, $-X_3$-alkynyl, $-X_5$-cycloalkyl, $-X_5$-heterocyclyl, $-X_5$-aryl and $-X_5$-heteroaryl;

$X_3$ is selected from a bond, O, S, and N-alkyl;

$X_5$ is selected from a bond, lower alkyl, O, S and N-alkyl; and wherein the degree of N-substitution is effective to lower the melt viscosity, the solution viscosity, or both, compared to the same polymer without N-substitution.

8. The polymer according to claim 7, wherein $R^8$ is an alkyl-terminated poly(alkylene oxide) selected from the group consisting of methoxy-terminated poly(ethylene glycols) (PEG) of molecular weight 100 to 10,000, methoxy-terminated poly(propylene glycols) (PPG) of molecular weight 100 to 10,000 and methoxy-terminated block copolymers of PEG and PPG of molecular weight 100 to 10,000.

9. The polymer according to claim 4, wherein at least one monomeric aromatic ring of formula (I) is substituted with iodine, so that the sum of y1 and y2 in formula (I) is greater than zero.

10. The polymer according to claim 7, wherein $R^8$ is OH.

11. The polymer according to claim 7, wherein $R^1$ is selected from:

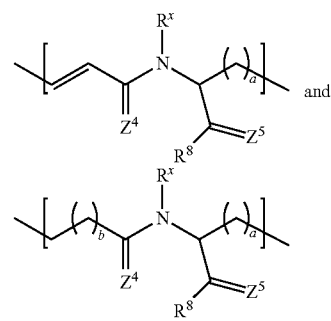

wherein $R^x$ is a $C_1$-$C_6$ alkyl group; $Z^4$ and $Z^5$ are each independently O or S; a and b independently range between 0 and 8, inclusive; $R^8$ is selected from the group consisting of H, OH, a therapeutically active moiety, a poly(alkylene oxide), —$X_3$—$C_1$-$C_{18}$ alkyl, —$X_3$-alkenyl, —$X_3$-alkynyl, —$X_5$-cycloalkyl, —$X_5$-hetero-cyclyl, —$X_5$-aryl and —$X_5$-heteroaryl;

$X_3$ is selected from a bond, O, S, and N-alkyl; and $X_5$ is selected from a bond, lower alkyl, O, S and N-alkyl.

12. A polymer according to claim 4, characterized by being a polycarbonate, polyarylate, polyiminocarbonate, polyphosphazene or polyphosphoester, comprising one or more recurring units having the structure of formula (Ia),

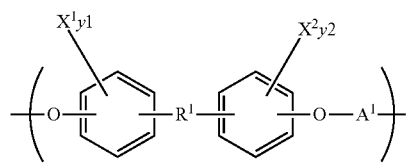
(Ia)

wherein $X^1$ and $X^2$ are each independently selected from Br and I; y1 and y2 are each independently zero or an integer in the range of 1 to 4, and $R^1$ is selected from the group consisting of substituted or unsubstituted, saturated or unsaturated, straight chain or branched aliphatic groups containing up to 48 carbon atoms, substituted or unsubstituted aromatic groups containing up to 48 carbon atoms, and substituted or unsubstituted araliphatic groups containing up to 48 carbon atoms in which the aliphatic portions are straight chain or branched and saturated or unsaturated, and $R^1$ contains from 2 to 8 heteroatoms selected from O, S and N, in which two of the heteroatoms form a polymer backbone amide group that is N-substituted with a $C_1$-$C_6$ alkyl group and $A^1$ is selected from the group consisting of:

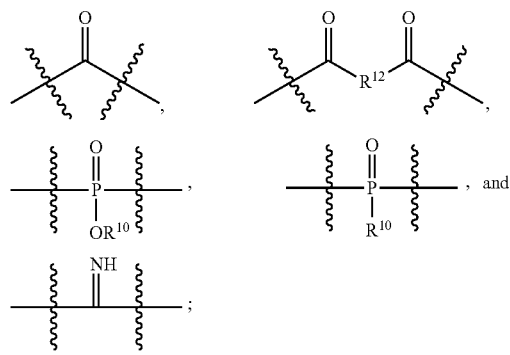

wherein $R^{10}$ is selected from H, $C_1$-$C_{30}$ alkyl, alkenyl or alkynyl and $C_2$-$C_{30}$ hetero-alkyl; heteroalkenyl or heteroalkynyl, and $R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylary or heteroalkynylaryl, $C_6$-$C_{30}$ alkylaryl, alkenylaryl or alkynylaryl, and $C_5$-$C_{30}$ heteroaryl; and wherein the degree of N-substitution is effective to lower the melt viscosity, the solution viscosity, or both, compared to the same polymer without N-substitution.

13. The polymer according to claim 4, further comprising recurring polyalkylene oxide block units comprising repeating units with the structure:

(III)

wherein B is —O—$((CHR^6)_p$—O$)_q$—; each $R^6$ is independently H or $C_1$ to $C_3$ alkyl; p is an integer ranging between one and four, inclusive; q is an integer ranging between about five and about 3000; and $A^2$ is the same as $A^1$.

14. A biocompatible, bioresorbable polymer comprising one or more recurring units of the formula:

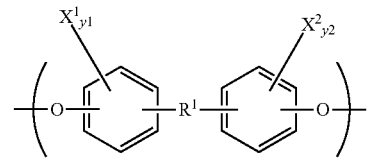

wherein $X^1$ and $X^2$ are each independently selected from Br and I; y1 and y2 are each independently zero or an integer in the range of 1 to 4, and $R^1$ is selected from the group consisting of substituted or unsubstituted, saturated or unsaturated, straight chain or branched aliphatic groups containing up to 48 carbon atoms, substituted or unsubstituted aromatic groups containing up to 48 carbon atoms, and substituted or unsubstituted araliphatic groups containing up to 48 carbon atoms in which the aliphatic portions are straight chain or branched and saturated or unsaturated, and $R^1$ contains from 2 to 8 heteroatoms selected from O, S and N, in which two of the heteroatoms form a polymer backbone amide group that is N-substituted with a $C_1$-$C_6$ alkyl group, and characterized by being a copolymer of a diphenol monomer that is not N-substituted.

15. An implantable drug delivery device comprising a therapeutically effective amount of a biologically or a physiologically active compound in combination with a biocompatible, bioresorbable polymer comprising a plurality of monomeric repeating units containing an amide group, wherein the amide groups comprise N-substituted amide groups and the N-substituents and degree of N-substitution are effective to lower the melt viscosity of said polymer, the solution viscosity of said polymer, or both, compared to the same polymer without N-substitution.

16. A polymer according to claim 12, further comprising recurring polyalkylene oxide block units comprising repeating units with the structure:

(III)

wherein B is —O—$((CHR^6)_p$—O$)_q$—; each $R^6$ is independently H or $C_1$ to $C_3$ alkyl; p is an integer ranging between one and four, inclusive; q is an integer ranging between about five and about 3000; and $A^2$ is the same as $A^1$.

17. The polymer of claim 12, characterized by being a copolymer of a diphenol monomer that is not N-substituted.

18. The polymer according to claim 5, wherein at least one monomeric aromatic ring of formula (I) is substituted with iodine, so that the sum of y1 and y2 in formula (I) is greater than zero.

19. The polymer according to claim 7, wherein at least one monomeric aromatic ring of formula (I) is substituted with iodine, so that the sum of y1 and y2 in formula (I) is greater than zero.

20. The polymer according to claim 12, wherein at least one monomeric aromatic ring of formula (I) is substituted with iodine, so that the sum of y1 and y2 in formula (I) is greater than zero.

21. The polymer according to claim 14, wherein at least one monomeric aromatic ring of formula (I) is substituted with iodine, so that the sum of y1 and y2 in formula (I) is greater than zero.

22. The polymer according to claim 5, further comprising recurring polyalkylene oxide block units comprising repeating units with the structure:

(III)

wherein B is $-O-((CHR^6)_p-O)_q-$; each $R^6$ is independently H or $C_1$ to $C_3$ alkyl; p is an integer ranging between one and four, inclusive; q is an integer ranging between about five and about 3000; and $A^2$ is the same as $A^1$.

23. The polymer according to claim 7, further comprising recurring polyalkylene oxide block units comprising repeating units with the structure:

(III)

wherein B is $-O-((CHR^6)_p-O)_q-$; each $R^6$ is independently or $C_1$ to $C_3$ alkyl; p is an integer ranging between one and four, inclusive; q is an integer ranging between about five and about 3000; and $A^2$ is the same as $A^1$.

24. The polymer according to claim 14, further comprising recurring polyalkylene oxide block units comprising repeating units with the structure:

(III)

wherein B is $-O-((CHR^6)_p-O)_q-$; each $R^6$ is independently H or $C_1$ to $C_3$ alkyl; p is an integer ranging between one and four, inclusive; q is an integer ranging between about five and about 3000; and $A^2$ is the same as $A^1$.

25. The polymer of claim 5, characterized by being a copolymer of a diphenol monomer that is not N-substituted.

26. The polymer of claim 7, characterized by being a copolymer of a diphenol monomer that is not N-substituted.

* * * * *